(12) United States Patent
Wu

(10) Patent No.: US 9,089,585 B2
(45) Date of Patent: Jul. 28, 2015

(54) **EXTRACTS OF *POLYGONUM MULTIFLORUM* THUNB, AND PREPARATION PROCESS AND USES OF THE SAME**

(75) Inventor: Rong-Tsun Wu, Taipei (TW)

(73) Assignee: NATIONAL YANG-MING UNIVERSITY, Taipei (TW)

(*) Notice: Subject to any disclaimer, the term of this patent is extended or adjusted under 35 U.S.C. 154(b) by 1751 days.

(21) Appl. No.: 11/893,551

(22) Filed: Aug. 15, 2007

(65) Prior Publication Data

US 2009/0074896 A1 Mar. 19, 2009

Related U.S. Application Data

(62) Division of application No. 10/646,270, filed on Aug. 22, 2003, now abandoned.

(51) Int. Cl.
*A61K 36/704* (2006.01)
*A61K 36/70* (2006.01)

(52) U.S. Cl.
CPC ............ *A61K 36/704* (2013.01); *Y10S 514/838* (2013.01)

(58) Field of Classification Search
IPC .......................................... A61K 36/70,36/704
See application file for complete search history.

(56) References Cited

U.S. PATENT DOCUMENTS

| 5,531,991 A | 7/1996 | Cheng et al. |
|---|---|---|
| 6,010,702 A | 1/2000 | Lee et al. |
| 6,200,569 B1 | 3/2001 | Cheng |
| 2003/0082152 A1* | 5/2003 | Hedrick et al. |
| 2003/0180395 A1* | 9/2003 | Bueter .......................... 424/725 |
| 2004/0014682 A1 | 1/2004 | Ravagnan et al. |

FOREIGN PATENT DOCUMENTS

| CN | 1306837 A | * | 8/2001 |
|---|---|---|---|
| KR | 2001070840 A | * | 7/2001 |
| KR | 2001077956 | * | 8/2001 |
| WO | WO-95/30427 | | 11/1995 |
| WO | WO 9903816 A1 | * | 1/1999 |
| WO | WO-01/91763 | | 12/2001 |
| WO | WO 0191763 A2 | * | 12/2001 |
| WO | WO-01/91764 | | 12/2004 |

OTHER PUBLICATIONS iChineseHerbs.com: Botanical Names of Herbs: Online, URL <http://www.ichineseherbs.com/cross_ref_of_names.html> accessed Sep. 9, 2014, 7 pages.*
NIH: Stem Cell Information; Online, URL <http://stemcells.nih.gov/info/basics/pp./basics4.aspx> 4 pages, accessed on Sep. 10, 2014.*
H.B. MacPhillamy: Drugs From Plants; Plant Science Bulletin, Botanical Society of America, vol. 9, No. 2, Apr. 1963.*
Phillipson, J. New Drugs From Nature—It Could Be Yew; Phytotherapy Research 13 (1999) pp. 2-8.*

(Continued)

*Primary Examiner* — Patricia A Leith
(74) *Attorney, Agent, or Firm* — Birch, Stewart, Kolasch & Birch, LLP

(57) ABSTRACT

Disclosed herein are processes for preparing extract products from the root of *Polygonum multiflorum* Thunb. and the extract products thus obtained, which are biologically active in promoting the proliferation, growth and/or differentiation of hematocytes and bone marrow cells in vitro and in vivo.

5 Claims, 15 Drawing Sheets

(56) References Cited

OTHER PUBLICATIONS

Raskin et al. Can an Apple a Day Keep the Doctor Away? Current Pharmaceutical Design, 2004, 10, 3419-3429.*

Revilla et al. Comparison of Several Procedures Used for the Extraction of Anthocynains From Red Grapes; J. Agric. Food Chem. 1998, 46, pp. 4592-4597.*

Smet et al. Herbal Remedies; N Engl J Med, vol. 347, No. 25, Dec. 19, 2002, pp. 2046-2205.*

Kimura at al., "Effects of stiilbene components of roots of *Polygonum* ssp. on liver injury in peroxidized oil-fed rats", Planta Medica (1983), 49(1): 51-4.

* cited by examiner

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial sequence
<220> FEATURE:
<223> OTHER INFORMATION: forward primer for beta-actin

<400> SEQUENCE: 1
gactacctac tgaagatcct                                           20

<210> SEQ ID NO 2
<211> LENGTH: 20
<212> TYPE: DNA
<213> ORGANISM: Artificial sequence
<220> FEATURE:
<223> OTHER INFORMATION: reverse primer for beta-actin

<400> SEQUENCE: 2
ccacatctga tggaaggtgg                                           20

<210> SEQ ID NO 3
<211> LENGTH: 25
<212> TYPE: DNA
<213> ORGANISM: Artificial sequence
<220> FEATURE:
<223> OTHER INFORMATION: forward primer for IL-1beta
```

```
<400> SEQUENCE: 3
atggcaactg ttcctgaact caact                                          25

<210> SEQ ID NO 4
<211> LENGTH: 26
<212> TYPE: DNA
<213> ORGANISM: Artificial sequence
<220> FEATURE:
<223> OTHER INFORMATION: reverse primer for IL-1beta

<400> SEQUENCE: 4
caggacaggt atagattctt tccttt                                         26

<210> SEQ ID NO 5
<211> LENGTH: 25
<212> TYPE: DNA
<213> ORGANISM: Artificial sequence
<220> FEATURE:
<223> OTHER INFORMATION: forward primer for IL-6

<400> SEQUENCE: 5
atgaagttcc tctctgcaag agact                                          25

<210> SEQ ID NO 6
<211> LENGTH: 24
<212> TYPE: DNA
<213> ORGANISM: Artificial sequence
<220> FEATURE:
<223> OTHER INFORMATION: reverse primer for IL-6

<400> SEQUENCE: 6
cactaggttt gccgagtaga tctc                                           24

<210> SEQ ID NO 7
<211> LENGTH: 21
<212> TYPE: DNA
<213> ORGANISM: Artificial sequence
<220> FEATURE:
<223> OTHER INFORMATION: forward primer for G-CSF

<400> SEQUENCE: 7
gcttcagctg gatgttgcca a                                              21

<210> SEQ ID NO 8
<211> LENGTH: 22
<212> TYPE: DNA
<213> ORGANISM: Artificial sequence
<220> FEATURE:
<223> OTHER INFORMATION: reverse primer for G-CSF

<400> SEQUENCE: 8
tctgctcagg tctaggccaa gt                                             22

<210> SEQ ID NO 9
<211> LENGTH: 21
<212> TYPE: DNA
<213> ORGANISM: Artificial sequence
<220> FEATURE:
<223> OTHER INFORMATION: forward primer for GM-CSF

<400> SEQUENCE: 9
ttcctgggca ttgtggtcta c                                              21
```

```
<210> SEQ ID NO 10
<211> LENGTH: 20
<212> TYPE: DNA
<213> ORGANISM: Artificial sequence
<220> FEATURE:
<223> OTHER INFORMATION: reverse primer for GM-CSF

<400> SEQUENCE: 10
tggattcaga gctggcctgg                                                   20

<210> SEQ ID NO 11
<211> LENGTH: 19
<212> TYPE: DNA
<213> ORGANISM: Artificial sequence
<220> FEATURE:
<223> OTHER INFORMATION: forward primer for SCF

<400> SEQUENCE: 11
tcttcaactg ctcctattt                                                    19

<210> SEQ ID NO 12
<211> LENGTH: 22
<212> TYPE: DNA
<213> ORGANISM: Artificial sequence
<220> FEATURE:
<223> OTHER INFORMATION: reverse primer for SCF

<400> SEQUENCE: 12
actgctacta ctgctgtcat tc                                                22
```

EXTRACTS OF *POLYGONUM MULTIFLORUM* THUNB, AND PREPARATION PROCESS AND USES OF THE SAME

CROSS-REFERENCE TO RELATED APPLICATION

This application is a divisional of U.S. application Ser. No. 10/646,270, filed Aug. 22, 2003, which is now abandoned.

BACKGROUND OF THE INVENTION

1) Field of the Invention

The present invention relates to methods for preparing extract products from the root of *Polygonum multiflorum* Thunb., to the extract products thus obtained, which have been demonstrated to have biological activities in enhancing liver cell regeneration and bone marrow stem cell proliferation, and to the uses of such extract products in the manufacture of medicaments for promoting cell proliferation, growth and/or differentiation.

2) Description of the Related Art

Stem cell refers to those cells capable of self-renewal and differentiation. Stem cells are most numerous during the embryonic period, and gradually decrease in number with aging. Thus, it was speculated that there is an important correlation/association between stem cells and aging. The stem cells in adults can generate a specific response toward the message in the environment, and generate new stem cells or differentiate into specific cells. When the stem cells receive a differentiation message, the stem cells rapidly reproduce in large amounts, and then finally proceed to differentiation. These stem cells are used for maintaining the balance of cells in adults, and replenish the number of cells that die due to natural causes or injuries.

The stem cells in bone marrow are divided into two types: (1) the hematopoietic stem cells which produce two more specialized types of stem cells, including lymphoid progenitor cells (which give rise to T and B lymphocytes) and myeloid progenitor cells (which give rise to leukocytes, erythrocytes, and megakaryocytes); and (2) the stromal cells which are the source of the cells making up the supporting structure in the bone marrow. The stromal cells have the characteristic of adhering to the bottom of plastic culture plates during culturing, and can differentiate into osteoblasts, chondrocytes, adipocytes, and even myoblasts. Stromal cells are required for the growth and differentiation of hematopoietic stem cells.

The production and number of stem cells will be extensively reduced as aging occurs, leading to various problems of aging, in which osteoporosis is the most common. The causes of osteoporosis include the loss of balance between bone formation and resorption. The osteoblastic cells derived from the osteoprogenitor cells are responsible for bone formation. Osteoprogenitor cells come from the stromal cells in the bone marrow. Dexamethasone and ascorbic acid can promote the proliferation growth of osteoprogenitor cells, and enable the cells to differentiate into matured osteoblasts. During the differentiating process, different markers of osteoblasts are expressed: There is the deposition of collagenous matrix first, and after 10 to 14 days, alkaline phosphatase (AP) is expressed.

Alkaline phosphatase is widely used as a biochemical marker for identification of osteoblast activity. While its actual function is unknown, it is currently believed that it participates in the skeletal mineralization process. After continuous culture to 21 days, the cells will secrete osteocalcein, and finally mineralize to form bone nodules.

It was known that the proliferation and differentiation of the stem cells would be affected by the growth factors, such as epidermal growth factor (EGF), granulocyte-monocyte colony stimulating factor (GM-CSF), etc. When the growth factors in the culture environment are changed, the stem cells differentiate into different cells along with the specificity of the growth factors. For example, GM-CSF can act on a specific receptor complex present on hematopoietic progenitor cells, and thus, can promote the proliferation and differentiation of the hematopoietic progenitor cells in the bone marrow into monocyte, neutrophil, etc. Therefore, GM-CSF may be used to treat the diseases related to leukocyte deficiency.

The recognition that somatic stem cells can be isolated and are able to renew a particular tissue motivated immediate efforts to apply these cells in the clinic. Bone marrow transplantation, albeit not successful in all circumstances, has become a mainstay in the treatment of hematological and some nonhematological diseases and cancers (Treleaven, J., and Barrett, J. 1992. *Introduction to bone marrow transplantation. In Bone marrow transplantation in practice.* J. Treleaven and J. Barrett, editors. Churchill Livingstone. New York, N.Y., USA. 3-9). Extensive skin lesions are now being treated with the use of autologous and even nonautologous grafts generated by the ex vivo expansion of epidermal cells (Green, H. (1989), *Lab. Invest.* 60:583-584). The reconstruction of damaged articular cartilage has been attempted using ex vivo expanded chondrogenic cells (Brittberg, M. et al. (1994), *N. Engl. J. Med.* 331:889-895). More recently, it has also been suggested that skeletal tissue, muscle, and even nervous tissue can be regenerated from stem cell populations. Potential applications extend beyond tissue regeneration, into the realm of gene transfer and gene therapy.

With the advance of molecular techniques, it is envisioned that stem cells could be engineered to replace or repair a defective gene. Because of their self-renewal and ability to regenerate a tissue, transgenic stem cells could provide a long-lasting clinical benefit to a recipient. Although the precise techniques for accomplishing these goals are not yet in hand, our biotechnological imaginations have run wild with the hope of recreating organs, correcting genetic diseases, and improving the quality of life as we age. The realization that cells with extensive potential for growth and differentiation occur in a variety of tissues also provides novel angles for understanding disease mechanisms. Since stem cells regulate the dynamics of normal tissues, a surprising range of disorders, including gastric atrophy, Alzheimer's disease, and, perhaps more intuitively, various forms of cancer, can be traced to altered stem cell function.

The trend toward defining stem cells primarily based on our ability to manipulate them in culture should also inspire us to devise novel models of these diseases, by analyzing genetically altered or carcinogen-treated stem cells either in vitro or in vivo after transplantation into host animals. Thus, even without improved tissue engineering or replacement, the study of stem cells may deepen our understanding of their pathogenic roles and facilitate the design of novel treatments.

The major causes of liver cirrhosis include chronic alcoholism, viral infection and metabolic lesion. Currently, there is no therapy that is effective in the treatment of liver cirrhosis. Recently, it is reported in literature that hepatocyte growth factor may be used in the treatment of human liver fibrosis and chronic liver failure (Matsuda Y. et al. (1995), *Journal of biochemistry,* 118 (3): 643-9; Ueki T et al. (1999), *Nature Medicine,* 5 (2): 226-30).

Mammalian hepatocytes have been used in the investigation of cell growth and differentiation mechanism for a long time. However, shortly after isolation, mammalian hepatocytes will lose their characteristics and their growth ability will be limited. Many researchers have endeavored to develop a methodology for the growth of normal hepatocytes, but no successful results have been reported.

Fleeceflower root is the dried root tuber of *Polygonum multiflorum* Thunb. (Family Polygonaceae), and it has been used as a traditional Chinese medicine called Heshouwu (Latin Title: *Radix Polygoni Multiflori*) for a long time.

Fleeceflower root is produced in most parts of China, in Taiwan and in Japan. It is collected in autumn and winter when leaves wither. After cutting off the two ends thereof, the collected fleeceflower root is washed clean, cut into pieces, and then dried. Fleeceflower root tastes sweet, astringent and bitter in flavor, slightly warm in nature, and it has affinity to the liver and kidney channels.

Fleeceflower root may be used in processed or unprocessed form. The processed fleeceflower root is slightly warm but not dry and not greasy. It functions in replenishing the liver and kidney, benefiting essence and blood, and astringing primordial energy. This herb is mild in action and very effective in tonification. It is said that anyone who takes this herb regularly for a long period can prolong his life. It serves to treat insufficiency of both the liver and kidney, deficiency of essence and blood, and disability of the lower-jiao. The unprocessed fleeceflower root can also function in clearing away toxins and lubricating the bowels, serving to treat scrofula, carbuncle and constipation due to dryness of the bowels.

Fleeceflower root is known to contain the following chemical components: emodin, chrysophanol, physcion, rhein, chrysophanol anthrone, resveratrol, piceid, 2,3,5,4'-tetrahydroxystilbene-2-O-β-D-glucopyranoside, 2,3,5,4'-tetrahydroxystilbene-2-O-β-D-glucopyranoside-2"-O-monogalloyl ester, 2,3,5,4'-tetrahydroxystilbene-2-O-β-D-glucopyranoside-3"-O-monogalloyl ester, gallic acid, catechin, epicatechin, 3-O-galloyl(−)-catechin, 3-O-galloyl(−)-epicatechin, 3-O-galloyl-procyanidin B-2, 3,3'-di-O-galloyl-procyanidin B-2, and β-sitosterol.

Fleeceflower root may be used in the treatment of hyperlipemia, lymphadenitis, carbuncles, urticaria with itching, and constipation.

It is reported in literature that hydroxyl anthraquinone derivatives contained in *Polygonum multiform* roots have the vasorelaxant effect (Huang, H. C. et al., *European Journal of Pharmacology* 198:211-3, 1993) and the effect of reducing the incidence of myocardial ischemia-reperfusion injury (Yim, T. K. et al., *Phytotherapy research* 14:195-99, 2000). It is also reported in literature that stilbene glucosides contained in *Polygonum multiform* roots have the blood lipid-lowering effect (Kimura Y, *Planta Medica* 49:51-54, 1983) and the antioxidation effect (Chen, Y. et al., *Journal of Agricultural and Food Chemistry* 47:2226-8, 1999).

WO 95/30427 disclosed the use of extracts of the Chinese herb *Polygonum multiflorum* in the treatment of hyperglycemia. According to the disclosure of WO9530427A1, the root of *Polygonum multiflorum* was extracted with 0.1 N $NH_4OH$ (20:1) (w/v) and centrifuged (1,000×g). The resultant supernatant was then applied to a Sephadex G-25 column and eluted with distilled deionized water. Three fractions were collected and demonstrated to exhibit a high insulin potentiating activity in fat cell assays and to have the effect of lowering blood sugar levels.

U.S. Pat. No. 6,200,569 disclosed and claimed a method for decreasing the glycosylated hemoglobin level or blood glucose level in a hyperglycemic patient, in which a water extract or a dilute acidic extract of *Polygonum multiform* roots, or *Cinnamomum* bark, or a mixture thereof, was administered to the patient. According to Example 2 of U.S. Pat. No. 6,200,569, the roots of *Polygonum multiform* were cut up and ground into small pieces, followed by extraction with water. The obtained water extract was then assayed for insulin potentiating activity.

CN 1306837A disclosed the use of *Polygonum multiform* roots and the extracts thereof in preventing and treating osteoporosis.

According to the Applicant's knowledge, none of the abovementioned patent publications and scientific articles has disclosed the production of methanol-extracted products of *Polygonum multiform* roots and the further extracted fractions thereof, as well as the biological effect(s) of these extracted products of *Polygonum multiform* roots upon bone marrow stem cells and liver cells.

SUMMARY OF THE INVENTION

Accordingly, in the first aspect, this invention provides a methanol-extracted product from the root of *Polygonum multiflorum* Thunb., which is prepared from a process comprising the steps of:
  (a) subjecting a suitable amount of a starting root material of *Polygonum multiflorum* Thunb. to a freezing treatment for a period of time;
  (b) subjecting a frozen product obtained in step (a) to an extraction treatment with methanol;
  (c) subjecting a resultant product from step (b) to a separating treatment to obtain a methanol solution free of extracted root debris of the starting root material of *Polygonum multiflorum* Thunb.; and
  (d) removing methanol from the methanol solution obtained in step (c) to obtain a methanol-extracted product.

The methanol-extracted product according to this invention has been analyzed to have a reverse-phase High Performance Liquid Chromatography (HPLC) elution profile as shown in FIGS. 1A to 1C.

In the second aspect, this invention provides a process for preparing a methanol-extracted product from the root of *Polygonum multiflorum* Thunb. comprising the steps of:
  (a) subjecting a suitable amount of a starting root material of *Polygonum multiflorum* Thunb. to a freezing treatment for a period of time;
  (b) subjecting a frozen product obtained from step (a) to an extraction treatment with methanol; and
  (c) subjecting a resultant product from step (b) to a separating treatment to obtain a methanol solution free of extracted root debris of the starting root material of *Polygonum multiflorum* Thunb.; and
  (d) removing methanol from the methanol solution obtained in step (c) to obtain a methanol-extracted product.

The thus obtained methanol-extracted product may be further extracted by dissolving the same in water and partitioning with n-hexane, so that a n-hexane-extracted product is obtained.

The water layer left from the above n-hexane extraction may be further extracted by partitioning with ethyl acetate, so that an ethyl acetate-extracted product is obtained.

The water layer left from the above ethyl acetate extraction may be further extracted by partitioning with n-butanol, so that a n-butanol-extracted product is obtained.

The above extract products, as well as the last water layer left from the n-butanol extraction, have been found to have more or less beneficial biological activities upon hepatocytes and bone marrow stem cells. Therefore, in the third aspect, this invention provides a pharmaceutical composition comprising as an active ingredient an extract product from the root of *Polygonum multiflorum* Thunb. as described above.

BRIEF DESCRIPTION OF THE DRAWINGS

The above and other objects and features of the present invention will become apparent with reference to the following description of the preferred embodiments taken in conjunction with the accompanying drawings, in which:

FIG. 1A: 312 nm, FIG. 1B: 254 nm, FIG. 1C: 280 nm; and in which the units of the x axis is "time (minutes)" and that of the y axis is "intensity (norm.);"

DETAILED DESCRIPTION OF THE INVENTION

Figure 1A:
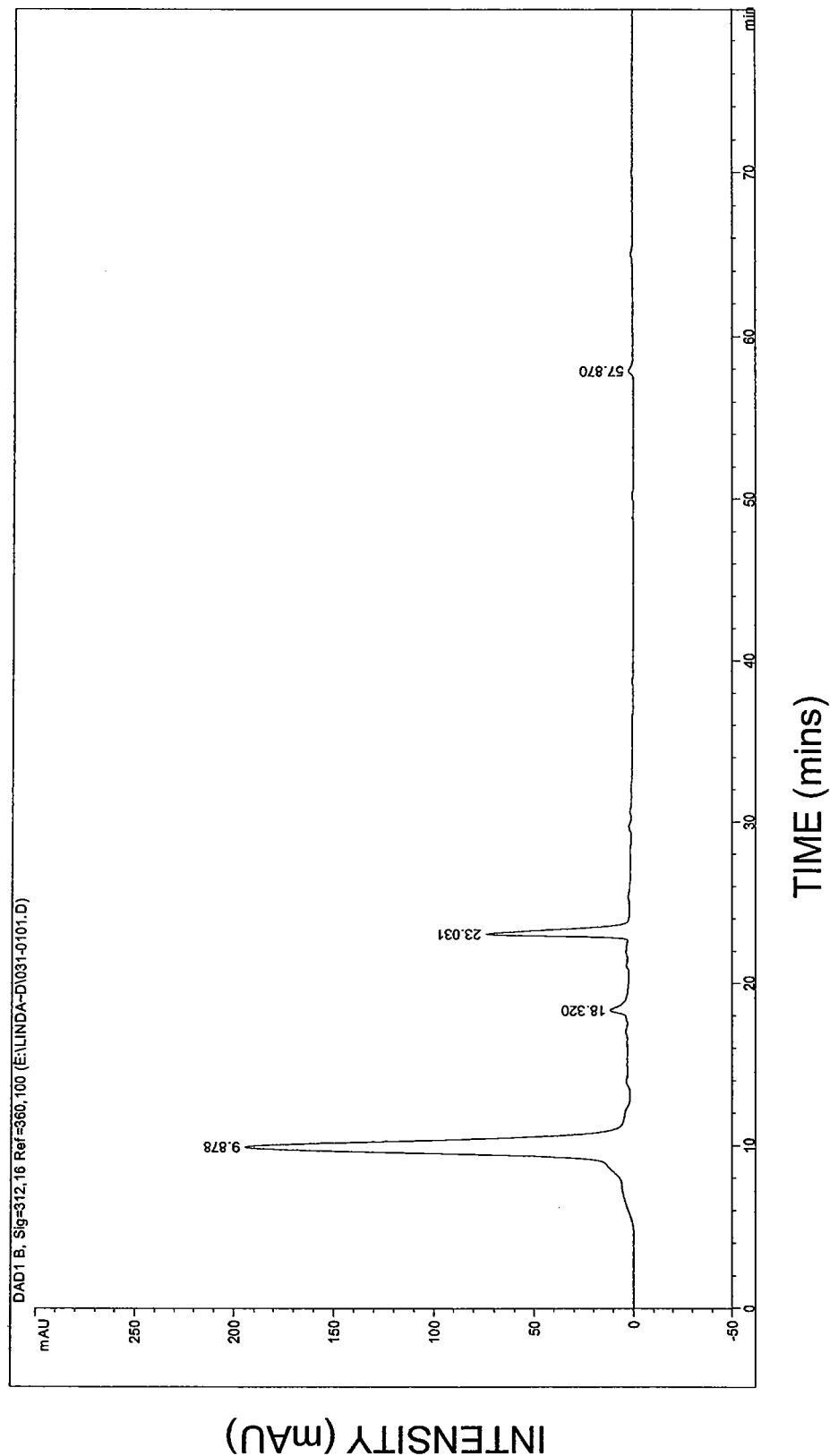
FIGS. 1A to 1C show the reverse-phase HPLC elution profiles of the methanol-extracted product of *Polygonum multiflorum* Thunb. (PoMuM) detected at three different wavelengths.

This invention provides extract products from the root of *Polygonum multiflorum* Thunb., which have been proved to be biologically active in promoting the proliferation and/or growth of heptatocytes and bone marrow cells. The extract products of this invention could be obtained by extracting the root of *Polygonum multiflorum* Thunb. with selected organic solvents in a specific order.

In particular, according to this invention, there is provided a process for preparing an extract product from the root of *Polygonum multiflorum* Thunb. comprising the steps of:
(a) subjecting a suitable amount of a starting root material of *Polygonum multiflorum* Thunb. to a freezing treatment for a period of time;
(b) subjecting a frozen product obtained in step (a) to an extraction treatment with methanol;
(c) subjecting a resultant product from step (b) to a separating treatment to obtain a methanol solution free of extracted root debris of the starting root material of *Polygonum multiflorum* Thunb.; and
(d) removing methanol from the methanol solution obtained in step (c) to obtain a methanol-extracted product.

The applicant surprisingly found that the freezing treatment of step (a) was necessary for the biological activities of the methanol-extracted product obtained from step (d). A possible reason might be that the freezing treatment assisted in stabilizing the processed root of *Polygonum multiflorum* Thunb.

Preferably, the starting root material of *Polygonum multiflorum* Thunb. used in step (a) is the processed form of Fleeceflower root, which is commercially available from traditional Chinese medicine markets. The processed root of *Polygonum multiflorum* Thunb. may be prepared by conventional processing procedures outlined in traditional Chinese medicine literature. Speaking briefly, the processed root of *Polygonum multiflorum* Thunb. may be traditionally prepared as follows: After cleaning the outer surfaces thereof, the roots of *Polygonum multiflorum* Thunb. are cut into thick slices or pieces and then admixed thoroughly with a black bean juice in a suitable nonferrous container. The resultant mixture is subjected to a stewing or steaming treatment until the thick slices or pieces of the roots of *Polygonum multiflorum* Thunb. look to have a brown colour on all sides thereof. The thus treated slices or pieces of the roots of *Polygonum multiflorum* Thunb. are dried under the sun to partial dryness and then cut into smaller slices and dried. For 100 kg of slices (pieces) of the roots of *Polygonum multiflorum* Thunb., 10 kg of black bean is used and the black bean juice is prepared as follows: 10 kg of black bean is boiled in a sufficient quantity of water for about 4 hours and stewed to provide about 15 kg of juice. The bean residue is boiled again in water for about 3 hours and stewed to provide about 10 kg of juice. The collected juices are combined to yield about 25 kg of black bean juice.

Preferably, in step (a), the freezing treatment is conducted at a temperature ranging from −20° C. to −70° C. In a preferred embodiment of this invention, the freezing treatment is conducted at −70° C.

Preferably, in step (b), the frozen product obtained in step (a) is crushed and then immersed in methanol to allow extraction.

Preferably, the separating treatment in step (c) is conducted by suction filtration.

Preferably, in step (d), methanol is removed by evaporation in vacuo.

Preferably, the methanol-extracted product obtained in step (d) is further lyophilized.

Figure 1B:
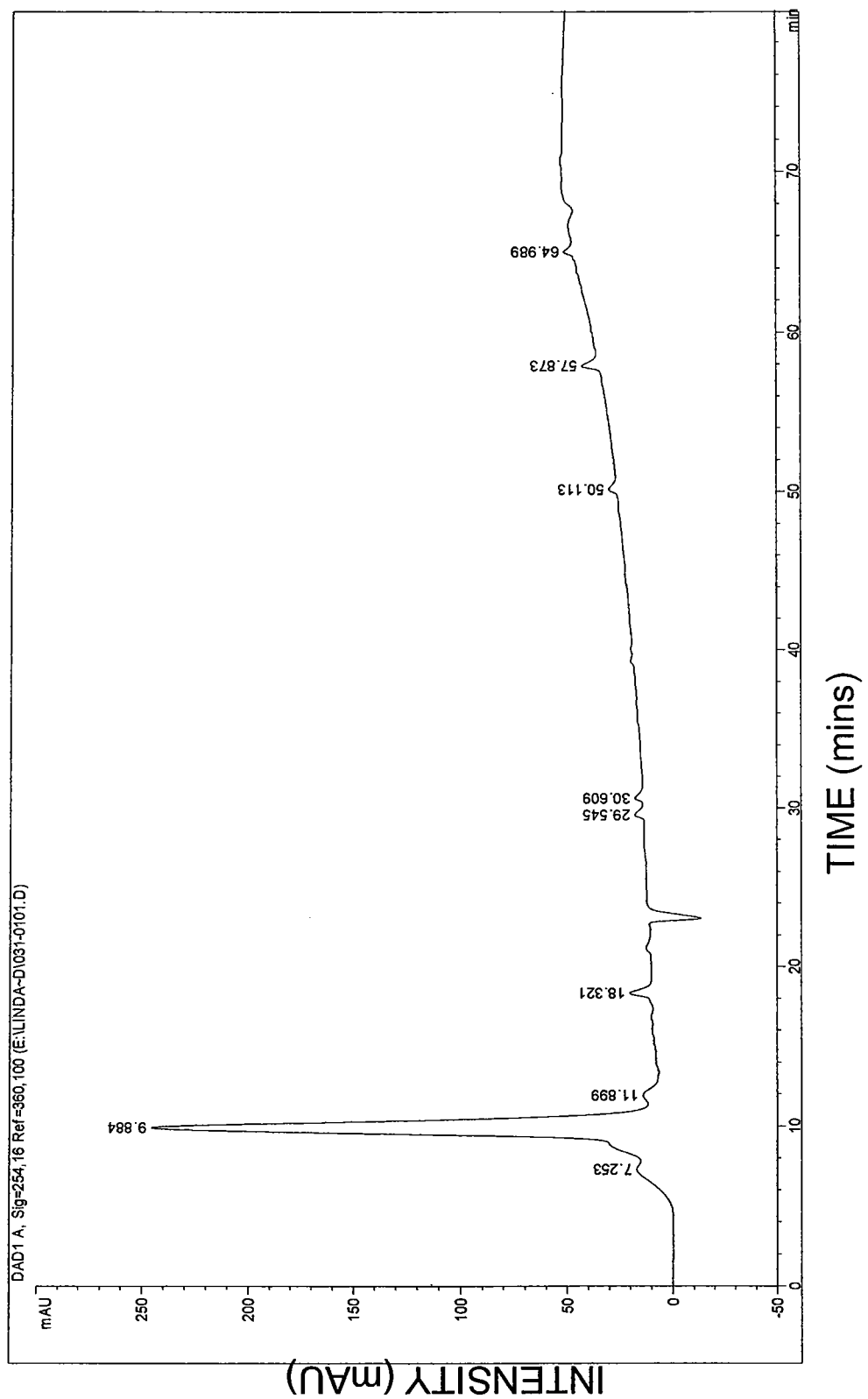
Figure 1C:
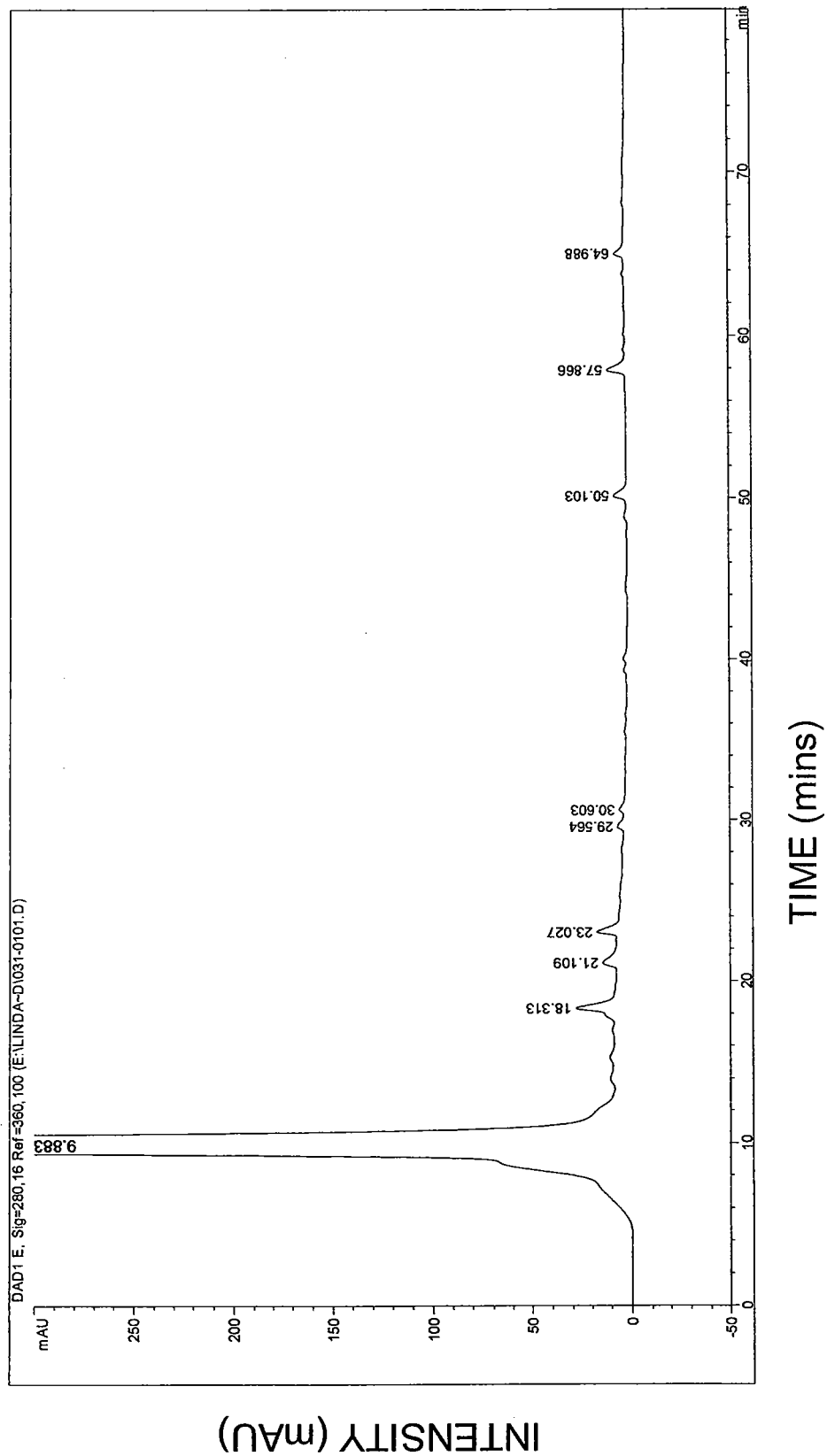

The methanol-extracted product obtained in step (d) has been analyzed by reverse-phase HPLC, and the obtained elution profile is shown in FIGS. 1A to 1C.

The methanol-extracted product obtained from step (d) may be further subjected to a n-hexane extraction treatment comprising the steps of:
(i) admixing the methanol-extracted product obtained from step (d) with a suitable amount of water;
(ii) partitioning a resultant mixture from step (i) with n-hexane to form a n-hexane layer and a water layer;
(iii) collecting the n-hexane layer formed in step (ii), and
(iv) removing n-hexane from the n-hexane layer collected in step (iii) to obtain a n-hexane-extracted product.

The water layer formed in step (ii) of the n-hexane extraction treatment may be further subjected to an ethyl acetate extraction treatment comprising the steps of:
(i') partitioning the water layer formed in step (ii) of the n-hexane extraction treatment with ethyl acetate to form an ethyl acetate layer and a water layer;
(ii') collecting the ethyl acetate layer formed in step (i'); and
(iii') removing ethyl acetate from the ethyl acetate layer collected in step (ii') to obtain an ethyl acetate-extracted product.

The water layer formed in step (i') of the ethyl acetate extraction treatment may be further subjected to a n-butanol extraction treatment comprising the steps of:
(i") partitioning the water layer formed in step (i') of the ethyl acetate extraction treatment with n-butanol to form a n-butanol layer and a water layer;
(ii") collecting the n-butanol layer formed in step (i"); and
(iii") removing n-butanol from the n-butanol layer collected in step (ii") to obtain a n-butanol-extracted product.

The applicant further exploited the biological activities of the extracted products thus obtained, as well as the water layer formed in step (i") of the n-butanol extraction treatment, and found that the extract products from the root of *Polygonum multiflorum* Thunb. according to this invention were effective in promoting the proliferation and/or growth of cells selected from the group consisting of hepatocytes, bone marrow stem cells, bone marrow stromal cells, bone marrow osteoprogenitor cells, bone marrow hematopoietic progenitor cells, bone marrow hematogenic cells, leukocytes and erythrocytes.

In addition, in order to determine whether or not the extract products from the root of *Polygonum multiflorum* Thunb. according to this invention could promote the proliferation of hepatocytes, the Applicant successfully developed a co-culture system of parenchymal and nonparenchymal cells from mouse liver.

Therefore, it is contemplated that the extract products from the root of *Polygonum multiflorum* Thunb. according to this invention can be used in the manufacture of pharmaceutical compositions for use in the treatment of a subject in need of proliferation of cells selected from the group consisting of hepatocytes, bone marrow stem cells, bone marrow stromal cells, bone marrow osteoprogenitor cells, osteoblasts, bone marrow hematopoietic progenitor cells, bone marrow hematogenic cells, leukocytes and erythrocytes.

For example, the pharmaceutical composition according to this invention may be used in the treatment of a subject afflicted with a liver disease selected from liver dysfunction, liver fibrosis and liver cirrhosis.

In addition, the pharmaceutical composition according to this invention may be used in the treatment of a subject afflicted with a disorder or disease associated with the deficiency of bone marrow stem cells, and the disorder or disease may be selected from the group consisting of aging, osteoporosis, cancer, anemia and leukopennia.

The pharmaceutical composition according to this invention may also be used in the treatment of a subject in need of restoration of bone marrow cells, wherein the subject is one selected from a hemodialysis patient, a patient receiving bone marrow transplantation therapy, and a cancer patient receiving irradiation therapy or chemotherapy or both.

The unit dosage form of the pharmaceutical compositions according to this invention may, in accordance with the object of a therapy, be suitably chosen from any one of oral preparations, injections, inhalants, nasal drops and the like. These unit dosage forms can each be prepared by a preparation method commonly known and used by those skilled in the art.

To produce an oral solid preparation, an excipient and, if necessary, a binder, a disintegrator, a lubricant, a coloring matter, a flavoring agent and/or the like may be admixed with an extract product from the root of *Polygonum multiflorum* Thunb. according to this invention. The resultant mixture can then be formed into tablets, coated tablets, granules, powder, capsules or the like by a method known per se in the art. Such additives can be those generally employed in the present field of art, including excipients: lactose, sucrose, sodium chloride, glucose, starch, calcium carbonate, kaolin, micro-crystalline cellulose, and silicic acid; binders: water, ethanol, propanol, sucrose solution, glucose solution, starch solution, gelatin solution, carboxymethylcellulose, hydroxypropylcellulose, hydroxypropylstarch, methylcellulose, ethylcellulose, shellac, calcium phosphate, and polyvinylpyrrolidone; disintegrators: dry starch, sodium alginate, powdered agar, sodium hydrogencarbonate, calcium carbonate, sodium lauryl sulfate, monoglycerol stearate, and lactose; lubricants: purified talc, stearate salts, borax, and polyethylene glycol; and corrigents: sucrose, bitter orange peel, citric acid, and tartaric acid.

To produce an oral liquid preparation, a flavoring agent, a buffer, a stabilizer and the like may be admixed with an extract product from the root of *Polygonum multiflorum* Thunb. according to this invention. The resultant mixture can then be formed into a solution for internal use, a syrup, an elixir or the like by a method known per se in the art. In this case, the flavoring agent can be the same as that mentioned above. Illustrative of the buffer is sodium citrate, while illustrative of the stabilizer are tragacanth, gum arabic, and gelatin.

To prepare an injection, a pH regulator, a buffer, a stabilizer, an isotonicity and the like may be admixed with an extract product from the root of *Polygonum multiflorum* Thunb. according to this invention. The resultant mixture can then be formed into a subcutaneous, intramuscular or intravenous injection by a method known per se in the art. Examples of the pH regulator and buffer include sodium citrate, sodium acetate, and sodium phosphate. Illustrative of the stabilizer include sodium pyrosulfite, ethylenediamine tetraacetic acid (EDTA), thioglycollic acid, and thiolactic acid. Examples of the isotonicity include sodium chloride and glucose.

The dosage of the pharmaceutical composition according to the present invention varies depending on the age, body weight, conditions, unit dosage form, administration frequency and the like. In general, however, it is preferred to orally or parenterally administer to a subject a compound of this invention as an effective ingredient in an amount of about 20 to 1,000 mg per day in one or several dosages.

The present invention will be described in more detail with reference to the following examples, which are given for the purpose of illustration only and are not intended to limit the scope of the present invention.

Example 1

Preparation of Extract Product from *Polygonum Multiflorum* Thunb. Root (A). Preparation of Methanol-Extracted Product:

2 kg of processed *Polygonum multiflorum* Thunb. root, which was bought from a local traditional Chinese medicine market, was frozen at −70° C. overnight. The frozen product was then crushed and immersed in methanol at 4° C. overnight, and the resultant mixture was filtrated by suction filtration to remove the root tissue of *Polygonum multiflorum* Thunb. root, so that a methanol solution was collected. The processed *Polygonum multiflorum* Thunb. root was extracted with methanol for three times (2.7 L, 4 L, 4 L), and the collected methanol solutions were combined and evaporated in vacuo to remove methanol. The resultant product was subjected to lyophilization, so that a methanol-extracted product, which was designated as PoMuM, was obtained in an amount of 661.5 g.

Reverse-phase HPLC analysis of PoMuM was conducted under the following conditions:
Column: NO. 10 Nucleosil C-18 5 μm (4.6×250 mm);
Mobile phase: 80% $H_2O$+20% MeOH+1% HAc gradient to 100% MeOH+1% HAc (60~80 min with 100% MeOH+1% HAc wash);
Flow rate: 0.8 ml/min; and
Inj. volume: 400 μg in 100 μl MeOH.

The reverse-phase HPLC elution profile of PoMuM was detected under 312 nm (FIG. 1A), 254 nm (FIG. 1B) and 280 nm (FIG. 1C), respectively, and the obtained results are shown in FIGS. 1A to 1C.

Different batches of PoMuM, which were prepared according to the above procedures, were detected by reverse-phase HPLC to have substantially the same elution profiles as that shown in FIGS. 1A to 1C. One batch of PoMuM was then subjected to further extraction as described in the following Preparation step (B), and the remaining batches were used in the following Examples to determine the biological activities of PoMuM.

(B). Preparation of n-Hexane-Extracted Product:

661.5 g of PoMuM as prepared from the above Preparation step (A) was admixed with 700 ml redistilled water, followed by addition of an equal amount of n-hexane to allow partitioning. The partitioning treatment was repeated four times, and the collected n-hexane layers were combined and evaporated in vacuo to remove n-hexane. The resultant residue was subjected to lyophilization, so that a n-hexane-extracted product, which was designated as PoMuMPh, was obtained in an amount of 10.6 g. The remaining water layer was subjected to further extraction as described in the following Preparation step (C).

(C). Preparation of Ethyl Acetate-Extracted Product:

The water layer obtained from the above Preparation step (B) was added with an equal amount of ethyl acetate to allow partitioning. The partitioning treatment was repeated three times, and the collected ethyl acetate layers were combined and evaporated in vacuo to remove ethyl acetate. The resultant residue was subjected to lyophilization, so that an ethyl acetate-extracted product, which was designated as PoMuMPe, was obtained in an amount of 35.0 g. The remaining water layer was subjected to further extraction as described in the following Preparation step (D).

D. Preparation of n-Butanol-Extracted Product:

The water layer obtained from the above Preparation step (C) was added with an equal amount of n-butanol to allow partitioning. The partitioning treatment was repeated four times, and the collected n-butanol layers were combined and evaporated in vacuo to remove n-hexane. A part of the resultant residue was subjected to lyophilization, so that a n-butanol-extracted product, which was designated as PoMuMPb, was obtained in an amount of 36.2 g.

Lastly, the remaining water layer was also subjected to lyophilization, so that a product, designated as PoMuMPw, was obtained in an amount of 416.2 g.

The respective amounts and yields of the above different extract products starting from 2 kg of processed *Polygonum multiflorum* Thunb. root were summarized in Table 1.

TABLE 1

|  | Amount (g) | Yield (%) |
| --- | --- | --- |
| PoMuM | 661.5 | 33.08 |
| PoMuPh | 10.6 | 0.53 |
| PoMuPe | 35.0 | 1.75 |
| PoMuPb | 36.2 | 1.81 |
| PoMuPw | 416.2 | 20.81 |

Example 2

Evaluation of the Effect of Extract of *Polygonum multiflorum* Thunb. Root Upon the Growth of Mouse Hepatocytes In Vitro Experimental Procedures:
A. Preparation and Culture of Parenchymal and Nonparenchymal Cells:

Livers from C3H/HeN mice (male, 10 weeks old) were used to isolate hepatocytes and nonparenchymal cells by the two-step liver perfusion method (Klaunig, J. E. et al. (1981), Mouse liver cell culture. I. Hepatocyte isolation. In Vitro. 17(10):913-25; Bhatia, S. N. et al. (1999), *FASEB J.* 13, 1883-1900).

Briefly, the mouse liver was first perfused in situ through the portal vein with a $Ca^{2+}$-free Hanks' solution containing 5 mM ethylene glycol-bix (β-aminoethyl ether)-N,N,N',N'-tetraacetic acid (EGTA) at 37° C. for 10 minutes, followed by perfusion with a 0.05% collagenase solution for 10 minutes at pH 7.4 at 37° C. The perfused liver was excised and dispersed in a cold Hanks' solution, and the resultant liver cell suspension was filtered through a double layer of gauze and divided into two fractions.

The first fraction was used to obtain highly enriched preparations of parenchymal cells via Percoll isodensity centrifugation. The cell viability was examined by trypan blue exclusion test. Hepatocytes preparations with viability higher than 95% were used in the experiments of this example.

A highly enriched preparation of nonparenchymal cells was prepared by centrifuging the second fraction at 150 g for 8 min to obtain a cell precipitate, which was subsequently washed and re-suspended in a cold Hanks' solution containing 10% FCS.

The mouse hepatocytes as prepared above were suspended at a density of $5 \times 10^3$ viable cells/150 µL Dulbecco modified Eagle medium (DMEM) culture medium containing 30 µg/ml L-proline, $10^{-7}$ M Dexamethasone and 5 µg/ml insulin supplemented with 10% fetal calf serum (FCS) and were then placed into each well of 1% gelatin-coated 96-well culture plates. After incubation at 37° C. under 95% air plus 5% $CO_2$ for 2-3 hrs, a monolayer of hepatocytes was formed and adhered on the bottom wall of each well. The medium and dead hepatocytes in each well were removed, and nonparenchymal cells in 10% FCS in DMEM at a density of $5 \times 10^4$ cells per well were added. After overnight incubation, the cells in each well were washed twice with PBS and maintained with 180 µl serum-free DMEM medium supplemented with 1 mg/ml galactose, 30 µg/ml L-proline, 0.5 µg/ml insulin, $10^{-7}$ M dexamethasone and 10 ng/ml EGF. The culture plates were placed in a 37° C. humidified incubator with 5% $CO_2$/95% air atmosphere and incubated for 1 hour before conducting the following assays.

B. Calcein AM Assay (*Free Radical Biology & Medicine*, 31: 659-669, 2001 and *Journal of Immunological Methods*, 226: 29-41, 1999):

Different concentrations (100 µg/ml, 10 µg/ml and 1 µg/ml) of the PoMuM extract obtained from Example 1 were added into the wells of the culture plates prepared in the above procedure (A), respectively. The control group was treated without addition of any tested extract. Three days later, the culture medium in each well of the culture plates was removed, and 100 µl fresh medium containing 6 µM Calcein AM fluorescein (Molecular Probes, Oregon, USA) was added into each well. After incubation at 37° C. for 40 minutes, the culture plates were placed into a fluorimeter and excited at 480 nm, followed by detecting the absorbance at 520 nm. Each experiment was conducted in duplicate, and n=6 wells for each group. The obtained experimental data were analyzed by Student's t-test.

The cell proliferation effect of a tested extract was expressed by proliferation index (i.e., the absorbance of the experimental group treated with the tested extract measured at 520 nm divided by the absorbance of the control group measured at 520 nm).

C. MTT Assay (*J. of Immunological Method*, 119: 203-210, 1989):

Different concentrations (100 µg/ml, 10 µg/ml and 1 µg/ml) of the five extracts obtained from Example 1 were added into the wells of the culture plates prepared in the above procedure (A), respectively. The positive control group was treated with 10% FCS, and the negative control group was treated with nothing.

Three days later, the culture medium in each well of the culture plates was removed, and 100 µl fresh medium containing 0.5 mg/ml MTT was added into each well. After incubation at 37° C. for 4 hrs, the wells of the culture plates were added with MTT lysis buffer (20% SDS in 50% DMF/50% $H_2O$) in an amount of 150 µl/well. The culture plates were allowed to stand overnight and then subjected to absorbance detection using a microplate reader at O.D. 550 nm-O.D. 690 nm with the MTT lysing buffer as the blank. Each experiment was conducted in duplicate, and n=6 wells for each group. The obtained experimental data were analyzed by Student's t-test.

The cell proliferation effect of a tested extract was expressed by proliferation index, which was calculated from the measured absorbance ($O.D._{550}$ minus $O.D._{690}$) of the experimental group treated with the tested extract divided by the measured absorbance of the negative control.

Results:

The effect of the methanol-extracted product of *Polygonum multiflorum* Thunb. root, i.e. PoMuM obtained from Preparation step (A) of Example 1, upon the proliferation of hepatocytes co-cultured with nonparenchymal cells was determined by Calcein AM assay. Three different concentrations of PoMuM (100 µg/ml, 10 µg/ml and 1 µg/ml) were tested, and the obtained results were shown in Table 2.

TABLE 2

Effect of PoMuM upon the proliferation of hepatocytes co-cultured with nonparenchymal cells as determined by Calcein AM assay.

| Conc. (µg/ml) | Proliferation index | P-value |
|---|---|---|
| Control | 1.00 | |
| 1 | 0.95 | |
| 10 | 1.18 | P < 0.001 |
| 100 | 1.33 | P < 0.001 |

It can be seen from Table 2 that PoMuM at a concentration of 10 µg/ml can effectively enhance the proliferation of mouse hepatocytes co-cultured with nonparenchymal cells. In view of the promising results shown in Table 1, all of the extract products of *Polygonum multiflorum* Thunb. root obtained in Example 1, i.e. PoMuM, PoMuMPh, PoMuMPe, PoMuMPb and PoMuMPw, were further tested by MTT assay. Three different concentrations of each extract (100 µg/ml, 10 µg/ml and 1 µg/ml) were tested, and the obtained results are shown in Table 3.

TABLE 3

Effects of different extracts of *Polygonum multiflorum* Thunb. root upon the proliferation of hepatocytes co-cultured with nonparenchymal cells as determined by MTT assay.

| Group | Conc. (µg/ml) | Proliferation index | P-value |
|---|---|---|---|
| Negative control | 0 | 1.00 | |
| Positive control | 10% FCS | 1.49 | P < 0.001 |
| PoMuM | 1 | 1.24 | P < 0.002 |
| | 10 | 1.22 | P < 0.002 |
| | 100 | 1.30 | P < 0.0001 |
| PoMuMPh | 1 | 0.78 | P < 0.01 |
| | 10 | 0.92 | P < 0.05 |
| | 100 | 1.32 | P < 0.001 |

TABLE 3-continued

Effects of different extracts of *Polygonum multiflorum* Thunb. root upon the proliferation of hepatocytes co-cultured with nonparenchymal cells as determined by MTT assay.

| Group    | Conc. (μg/ml) | Proliferation index | P-value    |
|----------|---------------|---------------------|------------|
| PoMuMPe  | 1             | 1.10                | $P < 0.05$ |
|          | 10            | 1.13                | $P < 0.05$ |
|          | 100           | 0.97                |            |
| PoMuMPb  | 1             | 1.00                |            |
|          | 10            | 1.07                |            |
|          | 100           | 0.96                |            |
| PoMuMPw  | 1             | 0.99                |            |
|          | 10            | 1.03                |            |
|          | 100           | 1.06                |            |

It can be seen from Table 3 that PoMuM at any tested concentration can effectively enhance the proliferation of hepatocytes co-cultured with nonparenchymal cells. In addition, PoMuMPh at a higher concentration (100 μg/ml) and PoMuMPe at a lower concentration (1 μg/ml and 10 μg/ml) can effectively enhance the proliferation hepatocytes co-cultured with nonparenchymal cells.

To further exploit the biological activity of the present extracts of *Polygonum multiflorum* Thunb. root, PoMuM was selected for test in the mouse liver cirrhosis model described in the following Example 3.

Example 3

Evaluation of the Effect of Extract of *Polygonum multiflorum* Thunb. Root in the Treatment of DMN-Induced Liver Cirrhosis in Mouse Experimental Procedures:

Dimethylnitrosamine (DMN) was used to establish a liver cirrhosis model in mice according to Matsuda Y. et al. (1995), *Journal of Biochemistry*, 118 (3): 643-9.

C3H/HeN mice (male, 20-25 g, 7-8 weeks old) were intraperitoneally injected with DMN at a dose of 8 mg/Kg body weight once a day on Day 1, Day 2, Day 3, Day 5, Day 8 and Day 9, respectively, and the DMN-treated mice were monitored for the production of ascites in the peritoneal cavities thereof. The production of ascites in the DMN-treated mice was observed around Day 12. Thereafter, the DMN-treated mice were orally administered daily with PoMuM obtained from Preparation step (A) of Example 1 at a dose of 40 mg/Kg, 200 mg/Kg and 1000 mg/Kg for a period of 120 days, and these mice were monitored for the survival thereof. The control group was treated with PBS (pH 7.4) intraperitoneally for 12 days.

Animals that died during the experiment and those which were still alive after the 120-day period of treatment were sacrificed, and their livers were taken out to conduct liver histopathological examination. The degree of liver damage caused by DMN was determined by the observed extent of liver fibrosis.

Results:

C3H/HeN mice (7-8 weeks old) were intraperitoneally injected with DMN to induce the production of ascites and the DMN-treated mice were observed to have a progressive increase of ascites around Day 12. These mice were then orally administered with 0 mg/kg (●), 1000 mg/kg (○), 200 mg/kg (▼) and 40 mg/kg (▽) of PoMuM (n=4 for each group), and the survival of mice was monitored daily. The observed results are shown in FIG. 2.

Figure 2:
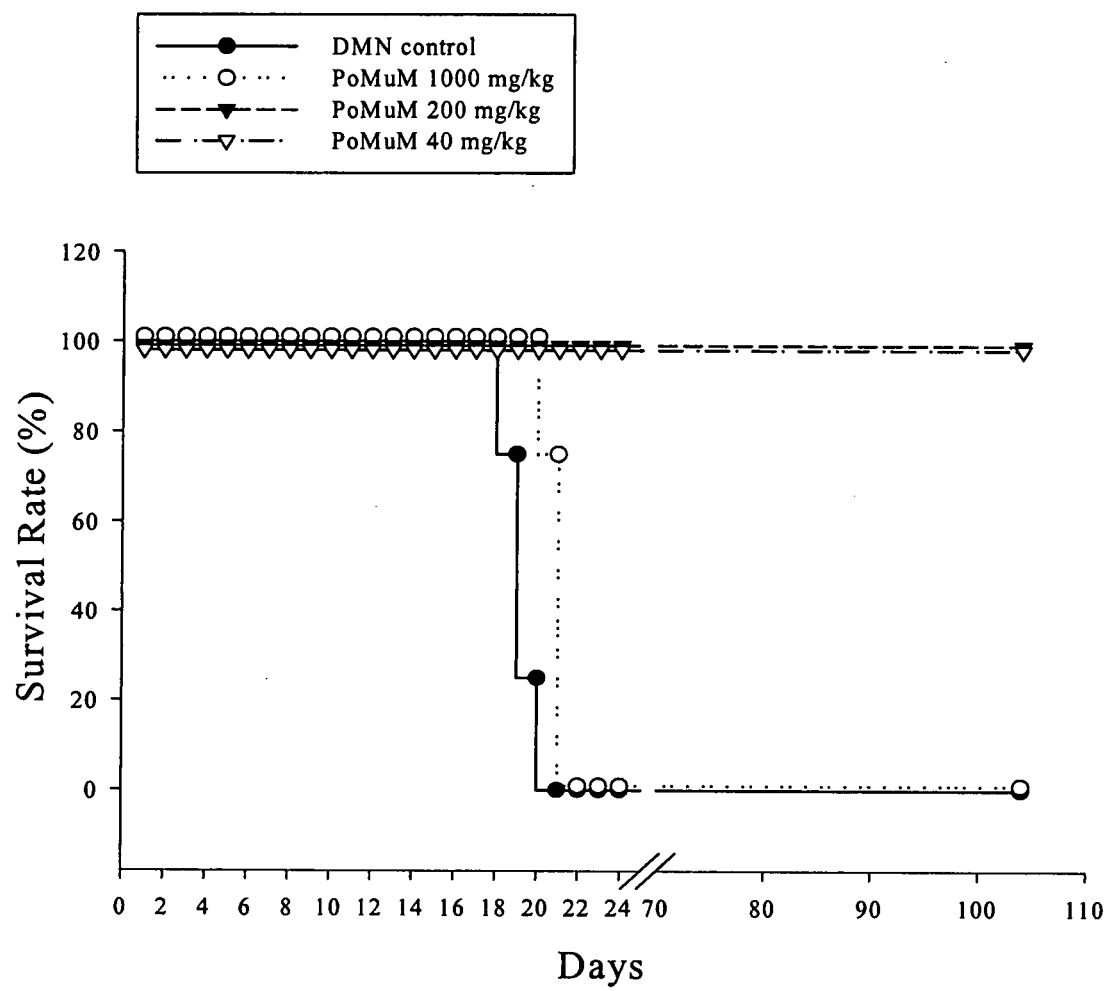
FIG. 2 shows the survival rates of dimethylnitrosamine (DMN)-treated mice, in which the mice were orally administered with 0 mg/kg (●), 1000 mg/kg (○), 200 mg/kg (▼) and 40 mg/kg (▽) of PoMuM (n=4 for each group) and survival of mice was monitored daily.

As can be seen from FIG. 2, all of the mice in the control group died around Day 18 to Day 21. In contrast, mice orally administered with either 40 mg/kg or 200 mg/kg of PoMuM were still alive after the treatment period of 120 days. Moreover, disappearance of ascites was observed in these mice.

Figure 3:
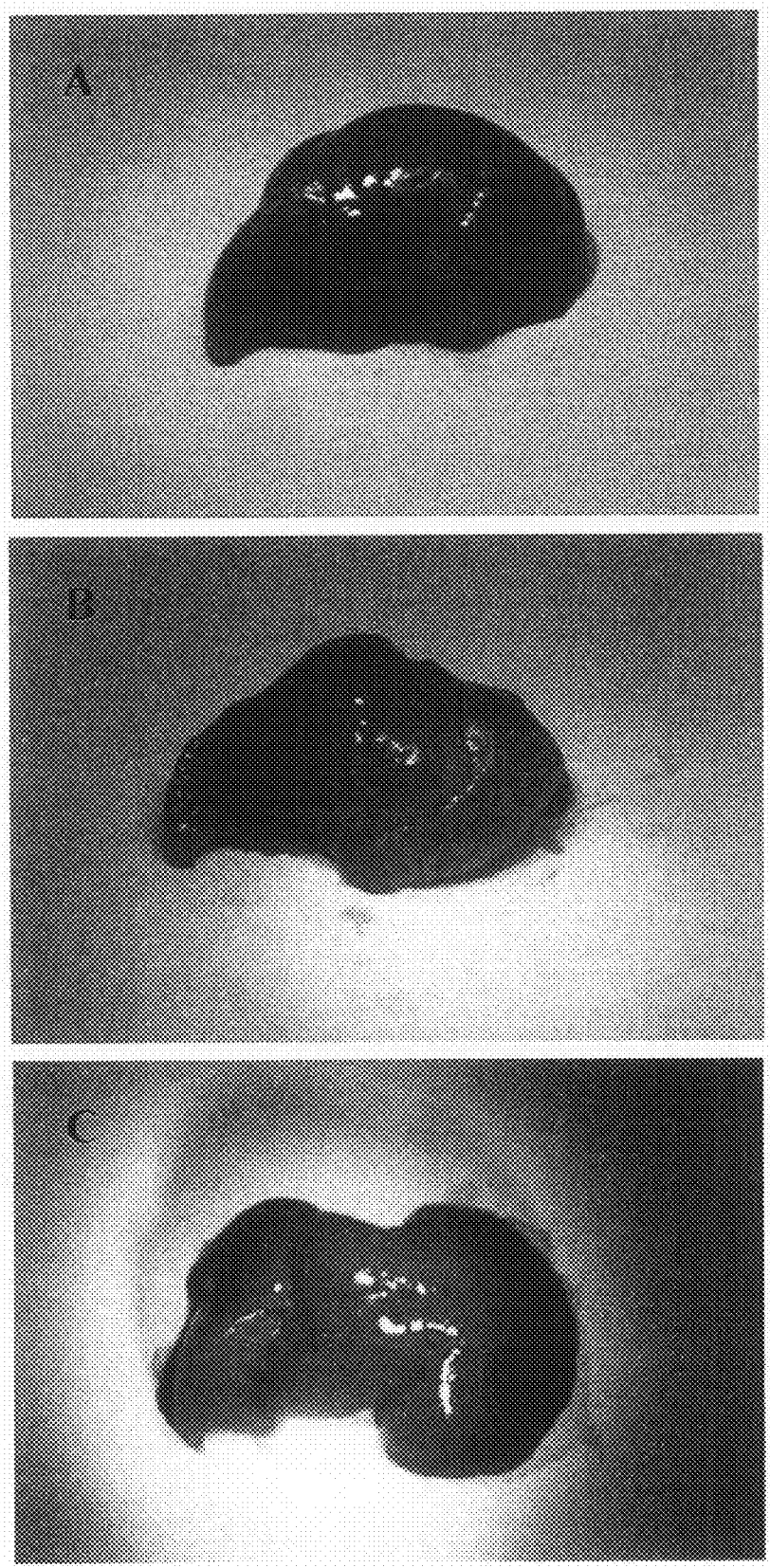
FIGS. 3 and 4 respectively show the gross views and the histopathological examination results of livers taken from three different mice, in which panel A: the liver of a mouse receiving Phosphate Buffered Saline (PBS) intraperitoneally for 12 days (control group); panel B: the liver of a mouse which received the DMN treatment as described in Example 3 for 12 days; and panel C: the liver of a mouse which received the DMN treatment as described in Example 3 for 12 days, followed by oral administration of 40 mg/kg PoMuM for 28 days.
Figure 4:
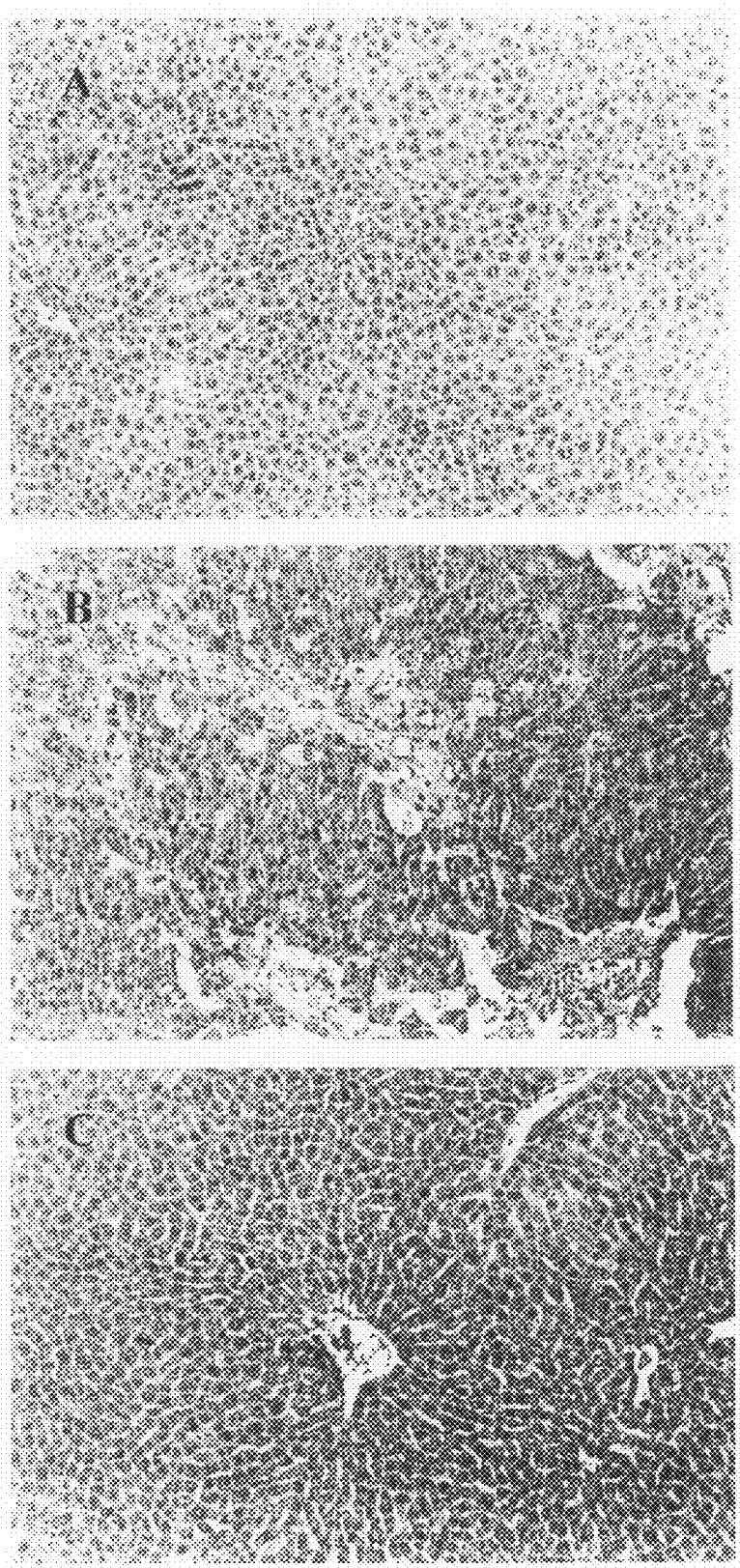

FIGS. 3 and 4 respectively show the gross views and the histopathological examination results of livers taken from three different mice, in which panel A represents the liver of a mouse receiving PBS intraperitoneally for 12 days (control group); panel B represents the liver of a mouse which received the DMN treatment as described in Example 3 for 12 days; and panel C represents the liver of a mouse which received the DMN treatment as described in Example 3 for 12 days, followed by oral administration of 40 mg/kg PoMuM for 28 days.

As can be seen from FIGS. 3 and 4, significant liver fibrosis and cirrhosis was observed in the liver of the mouse receiving the DMN treatment. In contrast, liver regeneration was observed in the liver taken from the mouse receiving PoMuM treatment (panel C in FIG. 3) and the loci where liver fibrosis had occurred appeared to be faint (panel C in FIG. 4).

It was noted that a high dose of PoMuM (1000 mg/kg) failed to provide a satisfactory liver protection effect to the DMN-treated mice, and this may be due to an over-dose effect thereof.

Example 4

Evaluation of the Effect of Extract of *Polygonum multiflorum* Thunb. Root Upon the Growth of Mouse Bone Marrow Stromal Cells In Vitro Experimental Procedures:
(I). Preparation of Mouse Bone Marrow Cells:

Under sterile condition, C57BL/6j (male, 15-20 g, 4-6 weeks old) were sacrificed, and their femoral bones were injected with DMEM/F12 culture medium (Gibco, N.Y. USA) so as to flush out the bone marrow cells. The collected cells in DMEM/F12 culture medium were then filtered through a sterile No. 53 nylon mesh so as to obtain a single cell suspension, the cell concentration of which was subsequently adjusted to $6 \times 10^5$ cells/ml with DMEM/F12 culture medium containing N2 supplement (Sigma, Mo., USA).
(II). Cell Proliferation Test of Mouse Bone Marrow Stromal Cells in the Presence of EGF:

The stimulation of bone marrow cells with epidermal growth factor (EGF) was conducted according to Owen M. E. et al. (1987), *Journal of Cell Science*, 87: 731-8.

The mouse bone marrow cells ($1.5 \times 10^5$ nucleated cells/well) as prepared in the above Procedure (I) were placed into 96-well culture plates and incubated in 200 μl of a defined medium (DMEM/F12 plus N2 supplement) supplemented with EGF (at a final concentration of 10 ng/ml). After incubation at 37° C. for 24 hrs, different concentrations (0.01 μg/ml, 0.1 μg/ml, 1 μg/ml, 10 μg/ml and 100 μg/ml) of the extracts of *Polygonum multiflorum* Thunb. root obtained in Example 1 were added into the wells of the culture plates, respectively. The positive control group was treated with 50 ng/ml EGF alone, and the negative control group was treated with 10 ng/ml EGF. The culture plates were then incubated in a 37° C. incubator containing 5% $CO_2$ for 96 hrs.

Subsequently, MTT assay was performed. Each well of the culture plates was added with a MTT solution (5 mg/ml dissolved in 1×PBS) to a final concentration of 1 mg/ml. Four hours later, each well of the culture plates was added with a MTT lysis buffer (20% sodium dodecyl sulfate (SDS) in 50% dimethylformamide (DMF)/50% $H_2O$) in an amount of 150

μl/well. The culture plates were allowed to stand for 14 hours and then subjected to absorbance detection using a microplate reader at O.D. 550 nm-O.D. 690 nm. Each experiment was conducted in duplicate, and n=6 wells for each group. The obtained experimental data were analyzed by Student's t-test.

(III). Morphological Observation of Mouse Bone Marrow Cell Culture by Liu's Staining:

The bone marrow cells ($1.0 \times 10^6$ nucleated cells/well) as prepared in the above Procedure (I) were placed into 12-well culture plates and incubated in 5 ml of a defined medium (DMEM/F12 plus N2 supplement) supplemented with EGF (at a final concentration of 10 ng/ml). After incubation at 37° C. for 24 hrs, extracts of *Polygonum multiflorum* Thunb. root with different concentrations (1 μg/ml, 10 μg/ml and 100 μg/ml) were added into the wells of the culture plates, respectively. The negative control group was treated with PBS. The culture plates were then incubated in a 37° C. incubator containing 5% $CO_2$ for 96 hrs. Thereafter, the cells were stained by Liu's staining, a modification of Gimesa staining (Stevens, M. L. *Fundamentals of clinical hematology*. W.B. Saunders company, 1997).

The culture medium in each well of the culture plates was removed, and the remaining cells were first stained by addition of 0.2 ml Liu's A solution (prepared by dissolving 0.18 g Eosin Y and 0.05 g Methylene blue in 100 ml methanol, followed by filtering the resultant solution through a No. 3 filter paper) for 45 seconds. Thereafter, 0.4 ml Liu's B solution (prepared by dissolving 0.12 g Methylene blue, 0.14 g Azure B, 2.52 g $Na_2HPO_4$ and 1.26 g $KH_2PO_4$ in 100 ml $H_2O$, followed by filtering the resultant solution through a No. 3 filter paper) was added into each well to mix with the Liu's A solution completely. After a reaction time of 90 seconds, each well was washed with water for three times so as to clean out the stain solution. The culture plates were air-dried and then examined under an optical phase microscope.

Results:

It is reported that EGF is a very important factor that influences the proliferation and differentiation of bone marrow stromal cells. EGF can promote the growth of bone marrow stromal cells. In addition, the presence of EGF in a primary culture of bone marrow cells could result in the proliferation of bone marrow cells while suppressing the differentiation of bone marrow cells to osteoblasts (Owen M. E. et al. (1987), *Journal of Cell Science*, 87: 731-8).

In this example, four extract products from the root of *Polygonum multiflorum* Thunb. as prepared in Example 1, i.e. PoMuMPh, PoMuMPe, PoMuMPb and PoMuMPw, were used to test their abilities in promoting the proliferation of bone marrow cells in the presence of EGF. The obtained results are summarized in Table 4.

TABLE 4

Effects of different extracts of *Polygonum multiflorum* Thunb. root upon the proliferation of EGF-stimulated bone marrow cells as determined by MTT assay.

| Group | Concentration | Proliferation index |
| --- | --- | --- |
| Negative control | 10 ng/ml EGF | 1.00 (±0.19) |
| Positive control | 50 ng/ml EGF | 1.26 (±0.13)* |
| PoMuMPh | 0.1 μg/ml | 1.17 (±0.22) |
|  | 1 μg/ml | 1.40 (±0.10)* |
|  | 10 μg/ml | 1.65 (±0.10)** |
|  | 100 μg/ml | 7.72 (±0.12)** |
| PoMuMPe | 0.01 μg/ml | 1.21 (±0.14) |
|  | 0.1 μg/ml | 1.06 (±0.05) |
|  | 1 μg/ml | 1.06 (±0.12) |
|  | 10 μg/ml | 1.23 (±0.07)* |
|  | 100 μg/ml | 3.74 (±0.03)** |
| PoMuMPb | 0.01 μg/ml | 0.97 (±0.17) |
|  | 0.1 μg/ml | 0.96 (±0.02) |
|  | 1 μg/ml | 1.09 (±0.08) |
|  | 10 μg/ml | 1.22 (±0.09) |
|  | 100 μg/ml | 1.69 (±0.10)** |
| PoMuMPw | 0.01 μg/ml | 0.99 (±0.08) |
|  | 0.1 μg/ml | 1.08 (±0.08) |
|  | 1 μg/ml | 0.92 (±0.14) |
|  | 10 μg/ml | 0.93 (±0.08) |
|  | 100 μg/ml | 1.02 (±0.10) |

*$P < 0.05$;
**$P < 0.01$.

It can be seen from Table 4 that in a culture environment containing EGF and N2 supplement, the first three tested extracts can enhance the proliferation of bone marrow cells, in which PoMuMPh was shown to be the most potent extract. Specifically, the treatment of PoMuMPh at a dose of 10 μl/ml increased the proliferation of bone marrow cells by 1.65 fold as compared to the control group. More surprisingly, the treatment of PoMuMPh at a dose of 100 μl/ml increased the proliferation of bone marrow cells over 7 times as much as that of the control group.

Knowing that EGF could promote the growth of bone marrow stromal cells, Liu's staining was further conducted in this example in order to determine whether or not the tested extracts could result in a massive proliferation of bone marrow stromal cells.

Figure 5:
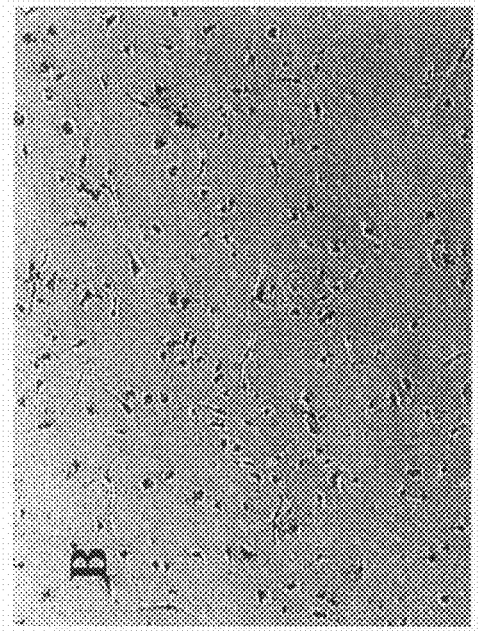
FIG. 5 shows the cell proliferative effect of n-hexane-extracted product from the methanol-extracted product of *polygonum multiflorum* Thunb. (PoMuMPh) upon the primary culture of bone marrow cells established from 4-6 week-old mice, in which panel A: vehicle; panel B: 1 μg/ml of PoMuMPh; panel C: 10 μg/ml of PoMuMPh; and panel D: 100 μg/ml of PoMuMPh (magnification 100×)
Figure 5:
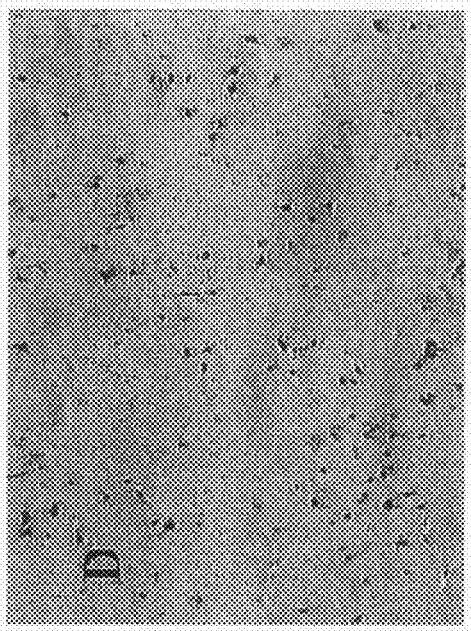
Figure 5:
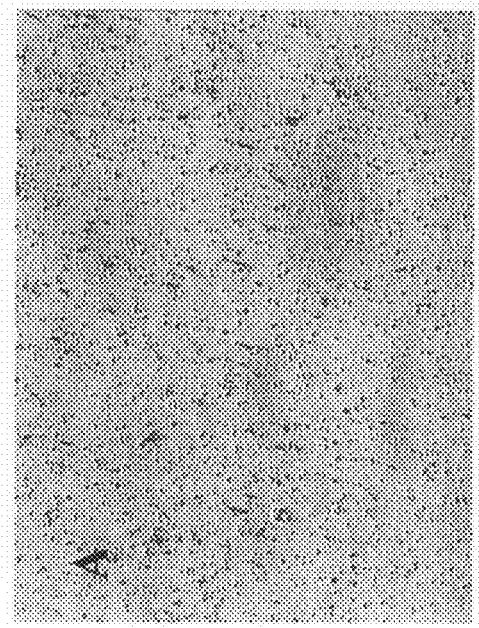
Figure 5:
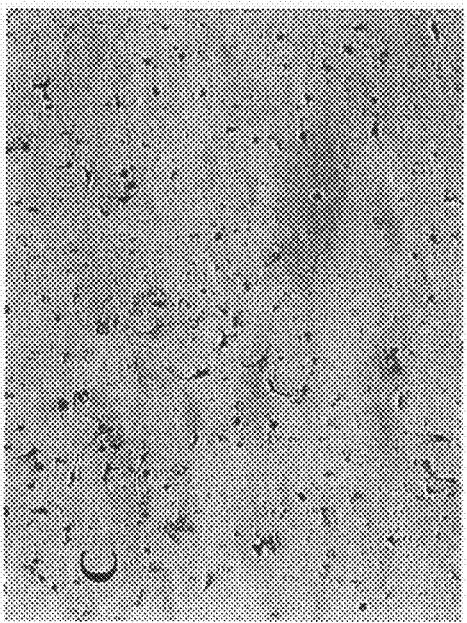

FIG. 5 shows the cell proliferative effect of PoMuMPh upon the primary culture of bone marrow cells established from 4-6 week-old mice, in which panel A represents a vehicle (PBS) control group, panel B represents a group tested with 1 μg/ml of PoMuMPh, panel C represents a group tested with 10 μg/ml of PoMuMPh, and panel D represents a group tested with 100 μg/ml of PoMuMPh (magnification 100×). It can be seen from FIG. 5 that a massive proliferation of bone marrow cells could be caused by the treatment of PoMuMPh. In addition, the number of adhered cells (stromal cells) was increased by PoMuMPh at a dose of 1 μg/ml or 10 μg/ml, while the number of non-adhered cells was increased by PoMuMPh at a dose of 100 μg/ml. Similar results were obtained using the three other extracts (data not shown). Based on the obtained results, it was believed that the extract products from the root of *Polygonum multiflorum* Thunb. according to this invention have the effect of promoting the proliferation of bone marrow cells, in particular bone marrow stromal cells.

Example 5

Evaluation of the Effect of Extract of *Polygonum multiflorum* Thunb. Root Upon the Maturation of Mouse Bone Marrow Osteoprogenitor Cells In Vitro Experimental Procedures:

(I). Preparation of Bone Marrow Cells:

Under sterile condition, C57BL/6j (male, 15-20 g, 4-6 weeks old) were sacrificed, and their femoral bones were injected with alpha-minimal essential medium (α-MEM) culture medium (Gibco, N.Y., USA) so as to flush out the bone marrow cells. The collected cells in α-MEM culture medium were then filtered through a sterile No. 53 nylon mesh so as to obtain a single cell suspension.

(II). Cell Maturation Test (A) of Mouse Bone Marrow Osteogenic Cells:

The mouse bone marrow cells ($1.5 \times 10^5$ nucleated cells/well) as prepared in the above Procedure (I) were placed into 96-well culture plates and incubated in α-MEM supplemented with 15% FCS, 10 μM dexamethazone, 50 μg/ml ascorbic acid, and 10 mM sodium, β-glycerophosphate. After incubation at 37° C. for 48 hrs, extracts of *Polygonum multiflorum* Thunb. root with different concentrations (0.01 μg/ml, 0.1 μg/ml, 1 μg/ml, 10 μg/ml, 100 μg/ml and 1000 μg/ml) were added into the wells of the culture plates, respectively. The positive control group was treated with 0.1 nM estrogen (Cheng, S. L. et al. (1994), *Endocrinology*, 134: 277-286), and the negative control group was treated with nothing. The culture plates were then incubated in a 37° C. incubator containing 5% $CO_2$ for 96 hrs. Subsequently, alkaline phosphatase (AP) colorimetry (Qu, Q. et al. (1998), *Bone*, 22: 201-209; Christenson, R. H. (1997), *Clinical Biochemistry*, 30: 573-593) was performed to observe the differentiation and maturation of osteogenic cells from the cultured bone marrow cells.

The alkaline phosphatase (AP) colorimetry (Aubin, J. E. et al. (1995), *Bone*, 17: 77S-83S; Sabokbar, A. et al. (1994), *Bone & Mineral*, 27: 57-67) was conducted as follows: The culture medium in each well of the culture plates was removed, and the remaining cells were added with 120 μl of 0.01% SDS and incubated in a 37° C. incubator for 10 minutes. Thereafter, 120 μl PNPP substrate solution (containing 0.5 M 2-amino-2-methyl-1-propanol (AMP), 2 mM $MgCl_2$, 2 mg/ml p-nitrophenyl phosphate, pH 10) was added into each well. After a reaction time of 10-15 minutes at 37° C., the culture plates were subjected to absorbance detection at O.D. 405 nm.

(III). Cell Maturation Test (B) of Mouse Bone Marrow Osteogenic Cells:

The mouse bone marrow cells ($2 \times 10^6$ cells/well) as prepared in the above Procedure (I) were placed into 24-well culture plates and incubated in α-MEM supplemented with 15% FCS, 10 μM dexamethazone, 50 μg/ml ascorbic acid, and 10 mM sodium β-glycerophosphate. After incubation at 37° C. for 48 hrs, extracts of *Polygonum multiflorum* Thunb. root with different concentrations (0.01 μg/ml, 0.1 μg/ml, 1 μg/ml, 10 μg/ml, 100 μg/ml and 1000 μg/ml) were added into the wells of the culture plates, respectively. The positive control group was treated with 0.1 nM estrogen, and the negative control group was treated with nothing. The culture plates were then incubated in a 37° C. incubator containing 5% $CO_2$ for 12 days (the culture medium was renewed every four days). Subsequently, Alizarin S staining was performed to observe the extent of calcium mineralization of the cultured cells.

The Alizarin S staining (*Endocrinology*, 138: 4456-4462, 1997) was conducted as follows: Cells were fixed with a 4% formalin solution for 10 minutes and then rinsed with distilled water twice. The fixed cells were stained with 2% Alizarin S (pH 4.1) (Sigma, Mo., USA) for 10 minutes and subsequently rinsed with absolute alcohol twice.

Results:

It is reported in literature that dexamethazone can direct the differentiation of mouse bone marrow cells toward osteoprogenitor cells. In addition, estrogen can promote the differentiation of mouse bone marrow stromal cells into osteoblasts in a culture environment containing dexamethazone, ascorbic acid and β-glycerophosphate, while increasing the extent of calcium mineralization of the cultured cells.

In this example, the five extract products from the root of *Polygonum multiflorum* Thunb. as prepared in Example 1, i.e. PoMuM, PoMuMPh, PoMuMPe, PoMuMPb and PoMuMPw, were used to test whether or not an extract product from the root of *Polygonum multiflorum* Thunb. according to this invention has the effect of promoting the maturation of dexamethazone-stimulated mouse bone marrow cells into osteoblasts.

Alkaline phosphatase is known to be a specific enzyme present on the cell membrane of a mature osteoblast. Therefore, in test (A) of this example, alkaline phosphatase colorimetry was employed in determining the maturation of osteoblasts from dexamethazone-stimulated bone marrow cells. The obtained results are summarized in Table 5.

TABLE 5

Effects of different extracts of *Polygonum multiflorum* Thunb. root upon the dexamethasone-stimulated osteogenic cell maturation of mouse primary bone marrow cell cultures

| Group | Concentration | AP activity index[a] |
|---|---|---|
| Negative control | | 1.00 (±0.08) |
| Positive control | 0.1 nM estrogen | 1.28 (±0.1)* |
| PoMuM | 1 μg/ml | 1.13 (±0.08)* |
| | 10 μg/ml | 1.67 (±0.15)** |
| | 100 μg/ml | 1.49 (±0.18)** |
| | 1000 μg/ml | 0.97 (±0.17) |
| PoMuMPh | 0.1 μg/ml | 1.15 (±0.36) |
| | 1 μg/ml | 1.37 (±0.19)* |
| | 10 μg/ml | 1.16 (±0.24) |
| | 100 μg/ml | 0.59 (±0.18)** |
| PoMuMPe | 0.01 μg/ml | 1.21 (±0.11)* |
| | 0.1 μg/ml | 1.36 (±0.06)** |
| | 1 μg/ml | 2.34 (±0.11)** |
| | 10 μg/ml | 1.34 (±0.09)** |
| | 100 μg/ml | 0.67 (±0.21)** |
| PoMuMPb | 0.01 μg/ml | 1.06 (±0.08) |
| | 0.1 μg/ml | 1.21 (±0.11)* |
| | 1 μg/ml | 1.52 (±0.23)** |
| | 10 μg/ml | 2.25 (±0.37)** |
| | 100 μg/ml | 1.18 (±0.13) |
| PoMuMPw | 0.1 μg/ml | 1.12 (±0.15) |
| | 1 μg/ml | 1.12 (±0.2) |
| | 10 μg/ml | 1.41 (±0.17)* |
| | 100 μg/ml | 1.1 (±0.2) |

[a]Data were analyzed by Student's t-test.
*$P < 0.05$;
**$P < 0.01$.

In test (A), the number of cells was determined by MTT reduction assay simultaneously. It is noted that under the culture conditions employed in test (A), the addition of the tested extracts at any concentration did not bring about any significant difference in regard to the proliferation of the cultured cells. However, it can be seen from Table 5 that the alkaline phosphatase activity of the dexamethasone-stimulated mouse bone marrow cells increased in the groups treated with the tested extracts. In addition, a significant extent of calcium mineralization was observed in test (B) (data not shown). Based on the obtained results, it is believed that the extract products from the root of *Polygonum multiflorum* Thunb. according to this invention have the effect of promoting the maturation of mouse osteoprogenitor cells into osteoblasts.

Example 6

Evaluation of the Effect of Extract of *Polygonum multiflorum* Thunb. root upon the Maturation of Mouse Bone Marrow Hematopoietic Progenitor Cells In Vitro Experimental Procedures:

(I). Erythropoietin (EPO)-Stimulation Test:

The mouse bone marrow cells ($1.5 \times 10^5$ nucleated cells/well) prepared according to the procedures set forth in Procedure (I) of Example 5 were placed into U-shaped 96-well culture plates and incubated in α-MEM supplemented with 1% bovine serum albumin (BSA), 7.5 μM 2-mecaptoethanol, 1.4 mM L-glutamine, 10 μM $FeCl_3$ and EPO (at a final concentration of 50 mU/well). After incubation at 37° C. for 24 hrs, extracts of *Polygonum multiflorum* Thunb. root with different concentrations (0.01 μg/ml, 0.1 μg/ml, 1 μg/ml, 10 μg/ml, 100 μg/ml and 1000 μg/ml) were added into the wells of the culture plates, respectively. The positive control group was treated with EPO at a concentration of 500 mU/well, and the negative control group was treated with EPO at a concentration of 50 mU/well. The culture plates were then incubated in a 37° C. incubator containing 5% $CO_2$ for 96 hrs. Subsequently, a colorimetric assay for hemoglobin (Rosenthal, A. et al. (1985), *Experimental Hematology*, 13: 174-184; Worthington, R. E. et al. (1987), *Experimental Hematology*, 15: 85-92) was performed to determine the extent of proliferation of mouse bone marrow hematopoietic progenitor cells.

The colorimetric assay for hemoglobin (Worthington, R. E. et al. (1987), *Experimental Hematology*, 15: 85-92) was conducted as follows: The U-shaped culture plates were centrifuged at 25° C. and 1000 rpm for 5 minutes. After removal of culture medium, a 50 μl Lysis buffer (0.01% NP-40 in distilled water) was added into each well and mixed well at room temperature. Subsequently, a 150 μl DAF reaction solution was added. After a reaction time of 5 minutes, the culture plates were subjected to absorbance detection at O.D. 620 nm.

(II). Granulocyte-Monocyte Colony Stimulating Factor (GM-CSF)-Stimulation Test:

The mouse bone marrow cells ($1.5 \times 10^5$ nucleated cells/well) prepared according to the procedures set forth in Procedure (I) of Example 5 were placed into 96-well culture plates and incubated in RPMI supplemented with 5% FCS and mGM-CSF (at a final concentration of 2 ng/ml). After incubation at 37° C. for 24 hrs, extracts of the *Polygonum multiflorum* Thunb. root with different concentrations (0.1 μg/ml, 1 μg/ml, 10 μg/ml and 100 μg/ml) were added into the wells of the culture plates, respectively. The positive control group was treated with 20 ng/ml mGM-CSF, and the negative control group was treated with 2 ng/ml mGM-CSF. After incubation in a 37° C. incubator containing 5% $CO_2$ for 96 hrs, the culture plates were subjected to MTT assay as described in Procedure (II) of Example 4 to determine the extent of cell proliferation.

Results:

It was learnt from our preliminary experiments that differentiation of mouse bone marrow cells toward hematopoietic progenitor cells could be enhanced in a suitable culture environment containing erythropoietin. In test (I) of this example, four extract products from the root of *Polygonum multiflorum* Thunb. as prepared in Example 1, i.e. PoMuMPh, PoMuMPe, PoMuMPb and PoMuMPw, were used to test whether or not an extract product from the root of *Polygonum multiflorum* Thunb. according to this invention had the effect of promoting the maturation of EPO-stimulated mouse bone marrow cells into erythrocytes. The obtained results are summarized in Table 6.

TABLE 6

Effects of different extracts of *Polygonum multiflorum* Thunb. on the EPO-stimulated erythropoiesis of mouse primary bone marrow cultures.

| Group | Concentration | Hb colorimetry index[a] |
|---|---|---|
| Negative control | EPO, 50 mU/well | 0.00 (±0.08) |
| Positive control | EPO, 500 mU/well | 1.64 (±0.19)** |
| PoMuMPh | 0.01 μg/ml | 1.56 (±0.12)** |
|  | 0.1 μg/ml | 2.14 (±0.1)** |
|  | 1 μg/ml | 1.93 (±0.18)** |
|  | 10 μg/ml | 2.04 (±0.13)** |
|  | 100 μg/ml | 1.36 (±0.25)* |
| PoMuMPe | 0.1 μg/ml | 1.5 (±0.31)* |
|  | 1 μg/ml | 1.6 (±0.15)** |
|  | 10 μg/ml | 2.78 (±0.12)** |
|  | 100 μg/ml | 2.01 (±0.2)** |
| PoMuMPb | 0.1 μg/ml | 1.08 (±0.12) |
|  | 1 μg/ml | 1.02 (±0.10) |
|  | 10 μg/ml | 1.56 (±0.03)** |
|  | 100 μg/ml | 1.62 (±0.05)** |
|  | 1000 μg/ml | 0.92 (±0.43) |
| PoMuMPw | 0.1 μg/ml | 1.03 (±0.07) |
|  | 1 μg/ml | 1.42 (±0.21)* |
|  | 10 μg/ml | 2.24 (±0.25)** |
|  | 100 μg/ml | 2.2 (±0.12)** |
|  | 1000 μg/ml | 1.3 (±0.19)* |

[a]Data were analyzed by Student's t-test.
*$P < 0.02$;
**$P < 0.001$.

As evident from Table 6, the extract products from the root of *Polygonum multiflorum* Thunb. according to this invention were effective in enhancing the proliferation and maturation of EPO-stimulated mouse bone marrow cells into erythrocytes.

In addition, it was known in the art that the presence of GM-CSF could promote the proliferation of bone marrow cells toward the hematopoietic progenitor cells, which in turn could be differentiated into granulocytes, monocytes, neutrophil, etc. In test (II) of this example, four extract products from the root of *Polygonum multiflorum* Thunb. as prepared in Example 1, i.e. PoMuMPh, PoMuMPe, PoMuMPb and PoMuMPw, were used to test whether or not an extract product from the root of *Polygonum multiflorum* Thunb. according to this invention had the effect of enhancing the proliferation of GM-CSF-stimulated mouse bone marrow cells. The obtained results are summarized in Table 7.

TABLE 7

Effects of different extracts of *Polygonum multiflorum* Thunb. on the mGM-CSF-stimulated proliferation of mouse primary bone marrow cultures.

| Group | Concentration | Proliferation index[a] |
|---|---|---|
| Negative control | mGM-CSF, 2 ng/ml | 1.00 (±0.04) |
| Positive control | mGM-CSF, 20 ng/ml | 2.05 (±0.06)** |
| PoMuMPh | 0.1 μg/ml | 0.94 (±0.03) |
|  | 1 μg/ml | 1.00 (±0.03) |
|  | 10 μg/ml | 1.13 (±0.07)** |
|  | 100 μg/ml | 1.38 (±0.04)* |
| PoMuMPe | 0.1 μg/ml | 1.07 (±0.05)* |
|  | 1 μg/ml | 1.04 (±0.07) |
|  | 10 μg/ml | 1.10 (±0.01)** |
|  | 100 μg/ml | 1.39 (±0.04)** |
| PoMuMPb | 0.1 μg/ml | 1.08 (±0.08) |
|  | 1 μg/ml | 1.15 (±0.04)** |
|  | 10 μg/ml | 1.11 (±0.09)* |
|  | 100 μg/ml | 1.20 (±0.07)** |

TABLE 7-continued

Effects of different extracts of *Polygonum multiflorum* Thunb. on the mGM-CSF-stimulated proliferation of mouse primary bone marrow cultures.

| Group | Concentration | Proliferation index[a] |
|---|---|---|
| PoMuMPw | 0.1 μg/ml | 1.03 (±0.05) |
|  | 1 μg/ml | 1.05 (±0.06) |
|  | 10 μg/ml | 1.05 (±0.08)** |
| * | 100 μg/ml | 1.12 (±0.02)** |

[a]Data were analyzed by Student's t-test.
*P < 0.05;
**P < 0.01.

As evident from Table 7, the extract products from the root of *Polygonum multiflorum* Thunb. according to this invention were effective in enhancing the proliferation of GM-CSF-stimulated mouse bone marrow cells.

Example 7

Evaluation of the Effect of Extract of *Polygonum multiflorum* Thunb. Root Upon the Proliferation of Mouse Bone Marrow Osteoprogenitor Cells In Vivo Experimental Procedures:

Based on the daily water consumption of mice, PoMuM prepared according to Example 1 was admixed with sterile distilled water at different doses (0 mg/Kg, 40 mg/Kg, 200 mg/Kg and 1000 mg/Kg). The thus prepared aqueous solutions were fed to C57BL/6j mice (male, 8-9 weeks old, and n=4 for each group) as daily drink ad libitum. After a dosing period of 5 days, these mice were sacrificed, and the bone marrow cells were taken from their femoral bones.

The collected bone marrow cells (at a cell density of $1.5 \times 10^5$ nucleated cells/well) were placed into 96-well culture plates and incubated in A-MEM supplemented with 15% FCS, dexamethazone (0.1 μM or 1 μM), 50 μg/ml ascorbic acid and 10 mM sodium β-glycerophosphate. After incubation in a 37° C. incubator containing 5% $CO_2$ for 96 hrs, the cultured cells were subjected to detection by alkaline phosphatase (AP) colorimetry as described in Procedure (II) of Example 5. Each experiment was conducted in duplicate.

Results:

Bone marrow cells taken from C57BL/6j mice, which had been administered with different doses (0, 40, 200 and 1000 mg/kg) of PoMuM for 5 days, were stimulated by dexamethasone and ascorbic acid so as to induce osteogenic cell maturation. Similar results were obtained in two independent experiments. The obtained results assessed by alkaline phosphatase colorimetry are summarized in FIG. 6.

Figure 6:
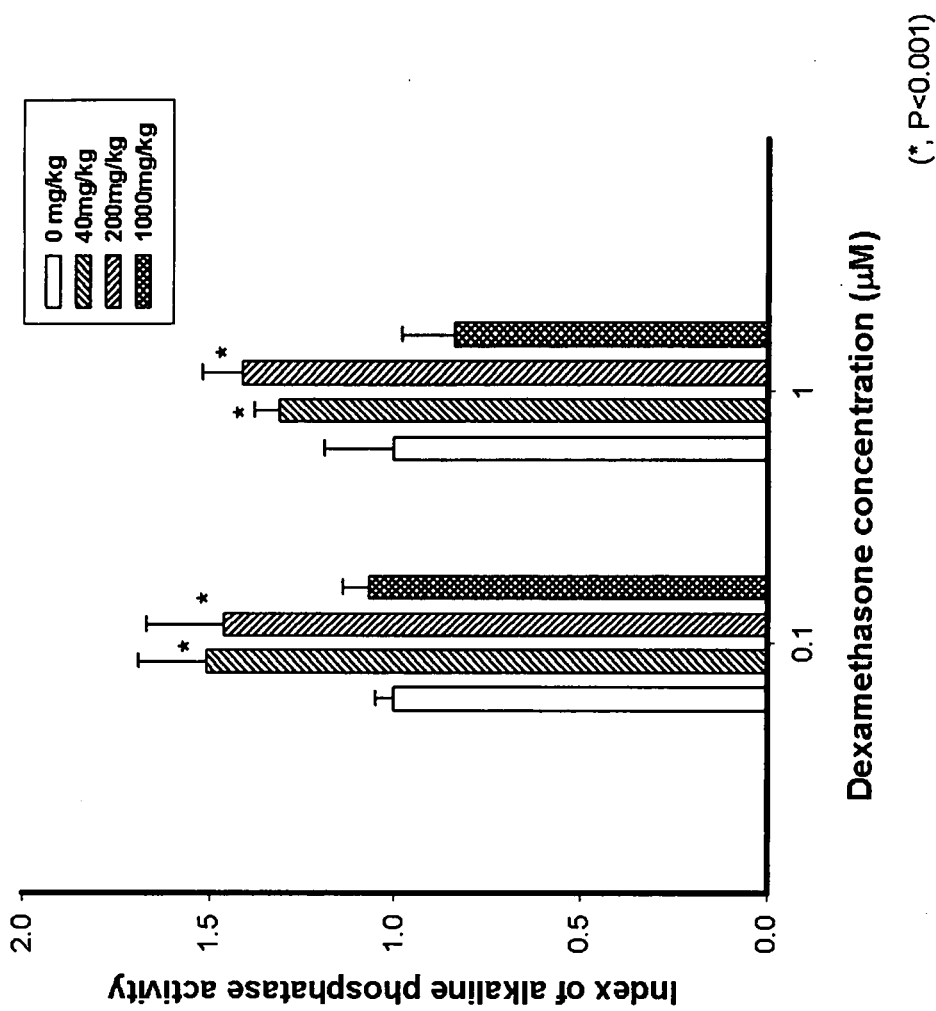
FIG. 6 is a bar diagram showing the effect of PoMuM in promoting the maturation of dexamethasone-stimulated mouse bone marrow cells taken from mice orally administered with different doses of PoMuM, in which the results were displayed as means±S.D. (n=4 for each group), and data were analyzed by Student's t-test (test group vs. control, *: $P<0.001$)

As shown in FIG. 6, a significant enhancement in osteogenic cell maturation was observed in respect to the test group fed with PoMuM at a dose of 40 mg/kg or 200 mg/kg. In connection with the test groups respectively fed with PoMuM at a dose of 1000 mg/kg, while no significance in statistics was observed as compared with the control group, an enhancement in osteogenic cell maturation was still exhibited.

Based on the experimental results collected so far, the extracts of *Polygonum multiflorum* Thunb. root according to this invention, which were proved to be effective in promoting the proliferation as well as differentiation of bone marrow cells, were believed to have potential in the development of medicines for use in the treatment of disorders or diseases associated with aging, e.g. osteoporosis in aged people due to a deficit in bone marrow osteogenic cells.

Example 8

Evaluation of the Effect of Extract of *Polygonum multiflorum* Thunb. Root Upon the Recovery of Mouse Bone Marrow Osteoprogenitor Cells In Vivo Experimental Procedures:

Based on the daily water consumption of mice, PoMuM prepared according to Example 1 was admixed with sterile distilled water at different concentrations (0 mg/Kg, 40 mg/Kg, 200 mg/Kg and 1000 mg/Kg).

BALB/c mice (female, 6-8 weeks old, and n=4 for each group) were intraperitoneally administered with two high doses of cyclophosphamide (CY) (200 and 100 mg/Kg) on Day 0 and Day 6, respectively, so as to induce a significant impairment to the bone marrow cells of said mice. These mice were fed with the respective aqueous solutions prepared above as daily drink ad libitum starting from Day 1. These mice were then sacrificed on Day 17, and the bone marrow cells were taken from their femoral bones.

The collected bone marrow cells (at a cell density of $1.5 \times 10^5$ nucleated cells/well) were placed into 96-well culture plates and incubated in A-MEM supplemented with 15% FCS, dexamethazone (0.1 μM or 1 μM), 50 μg/ml ascorbic acid and 10 mM sodium β-glycerophosphate. After incubation in a 37° C. incubator containing 5% $CO_2$ for 120 hrs, the maturation responses of the dexamethasone-stimulated mouse bone marrow cells were detected by alkaline phosphatase (AP) colorimetry as described in Procedure (II) of Example 5, so as to evaluate the cell maturation of osteoprogenic cells. Each experiment was conducted in duplicate.

Figure 7:
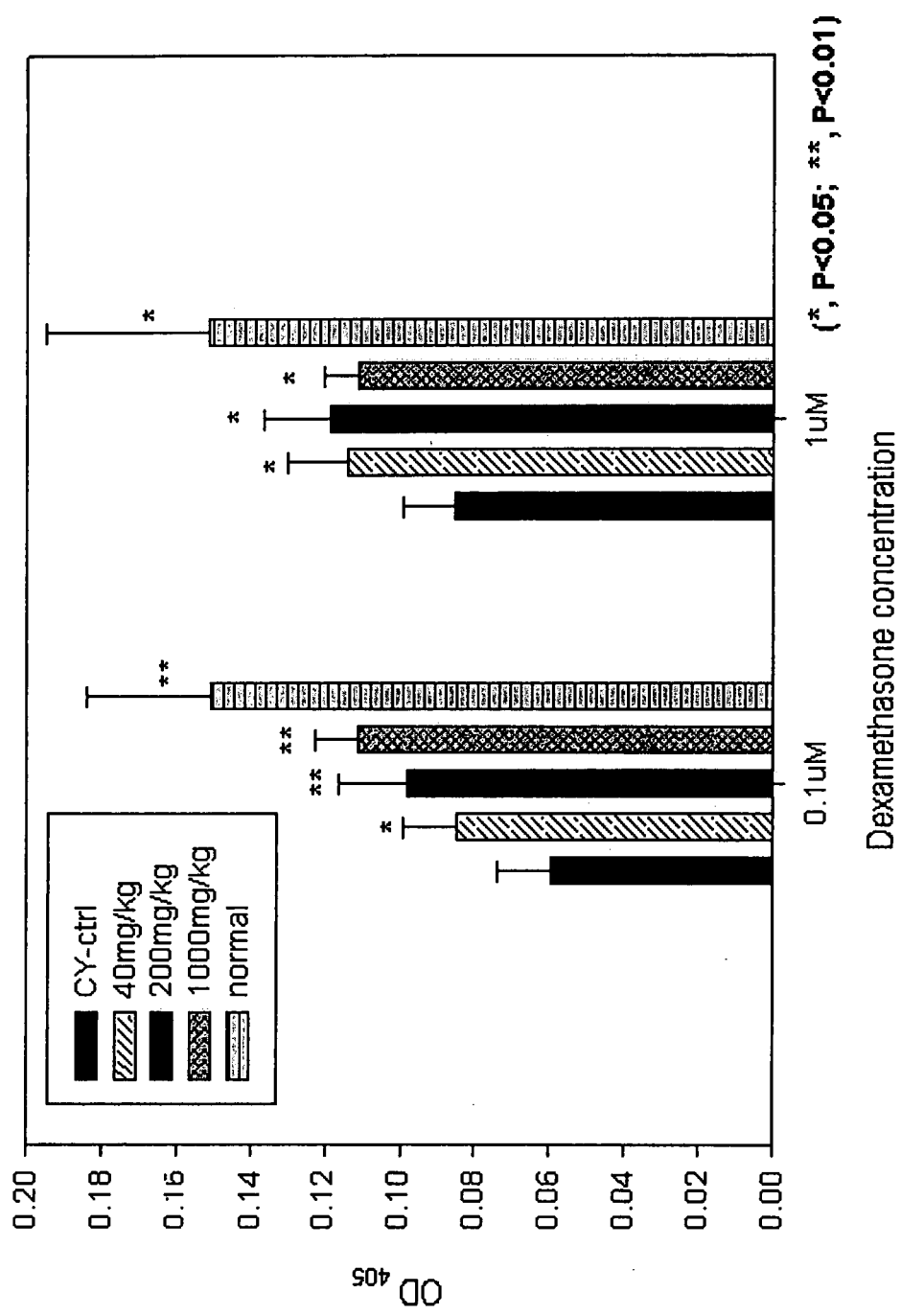
FIG. 7 is a bar diagram showing the effect of PoMuM in promoting the recovery of bone marrow cells in cyclophosphamide-treated mice, in which the results were displayed as means±S.D. (n=4 for each group), and data were analyzed by Student's t-test (test group vs. control, *: $P<0.05$ and **: $P<0.01$)

Results:

Cytotoxic substances could significantly impair the bone marrow cells, including the bone marrow osteoprogenic cells. Referring to FIG. 7, the bone marrow cells taken from mice of the CY control group were shown to have an alkaline phosphatase activity remarkably lower than that of the bone marrow cells taken from mice of the normal control group (without CY treatment). In addition, the detected alkaline phosphatase activities of the three PoMuM-treated groups were higher than that of the CY control group, suggesting that administration of PoMuM could promote the restoration of bone marrow cells in the CY-treated mice. Based on the obtained results, it is contemplated that the methanol-extracted products from the root of *Polygonum multiflorum* Thunb. according to this invention have the potential in developing medicines for use in the treatment of subjects in need of restoration of bone marrow cells, including hemodialysis patients, patients receiving bone marrow transplantation therapy, and cancer patients receiving irradiation therapy or chemotherapy or both, etc.

Example 9

Evaluation of the Effect of Extract of *Polygonum multiflorum* Thunb. Root Upon the Recovery of Mouse Bone Marrow Hematogenic Cells In Vivo Experimental Procedures:

Daily drinks containing different concentrations (0 mg/Kg, 40 mg/Kg, 200 mg/Kg and 1000 mg/Kg) of PoMuM were prepared in the same manner as described in Example 8.

On Day 0, C57/BL6j mice (female, 8-9 weeks old, and n=4 to 6 for each group) were intraperitoneally administered with cyclophosphamide (CY, dissolved in 0.9% NaCl) at a dose of 200 mg/Kg, so as to induce the occurrence of leukopenia in the CY-treated mice. One day after, the mice were fed with the respective daily drinks, which were replenished every two days. The normal group was i.p. treated with a 0.85% NaCl solution (0.2 ml), and the control group was the CY-treated group without treatment of the tested extract product. The mice were subjected to the following tests. Each experiment was conducted in duplicate.

(I). Cell Counting and Sorting of Leukocytes in Peripheral Blood (Owen, M. E. et al (1987), *Journal of Cell Science*, 87: 731-738):

This experiment investigates the effect of the methanol-extracted product from the root of *Polygonum multiflorum* (PoMuM) in promoting the recovery of leukocytes in cyclophosphamide-induced leukopenic mice (Ladisch, S. (1978), *Cancer Research*, 38: 1049-1051; Kaneko, M. et al. (1999), *Immunopharmacology*, 44: 223-231).

On Day 0, Day 2, Day 4, Day 7, Day 10 and Day 14, 0.1 ml of peripheral blood was sampled from the orbita of each of the mice and admixed with 25 µl of an EDTA solution (72 mg/ml) so as to prevent blood coagulation. The resultant whole blood sample was subjected to WBC counting and sorting as follows:

An aliquot of the whole blood sample was subjected to a 10-fold or 20-fold dilution with Turk's solution (2% acetic acid with 0.01% crystal violet) and then placed into a counting chamber for counting the number of leukocytes under a microscope with a magnification of 200×.

In the meantime, a drop of the whole blood sample was smeared on a slide glass and fixed and stained by Liu's staining essentially based on the procedures set forth in Procedure (III) of Example 4. The slide glass was then subjected to a differential cell count by microscopic examination (400× magnification). At least 100 leukocytes were microscopically examined for each sample.

(II). GM-CSF-Stimulation Test:

On Day 5 and 8, the mice in each group were sacrificed, and bone marrow cells taken therefrom were placed into 96-well culture plates at a cell density of $1.5 \times 10^5$ nucleated cells/well and incubated in RPMI supplemented with 5% FCS and mGM-CSF (at a final concentration of 4 ng/ml or 20 ng/ml). After incubation in a 37° C. incubator containing 5% $CO_2$ for 96 hrs, the culture plates were subjected to MTT assay as described in Procedure (II) of Example 4 to determine the extent of cell proliferation.

(III). Detection of Cytokine Expression by Reverse Transcription-Polymerise Chain Reaction (RT-PCR):

On Day 5, the mice in each group were sacrificed, and total mRNAs were extracted from the bone marrow cells collected therefrom. Five (5) µg of the extracted total mRNAs and 2.5 µg of oligo dT were mixed at 70° C. for 10 minutes and then placed at room temperature for 10 minutes. Subsequently, the mixture was added with 4 µl of 10 mM deoxyribonucleotide triphosphate (dNTP), 0.5 µl of rRNasin, and 1 µl AMV (Avian Myeloblastosis virus) reverse transcriptase (10 units) as well as the buffer thereof, so as to form a final reaction volume of 26.5 µl. The reverse transcription reaction was carried out by heating the mixture at 42° C. for 60 min, followed by heating at 90° C. for 5 min. Thereafter, 2.5 µl of cDNA formed therefrom was added with 0.5 µl 10 mM dNTP, the forward and reverse primers (for each primer, 1 µl in a concentration of 1 µg/µl) of a target cytokine (Interleukin-1β (IL-1β), Interleukin-6 (IL-6), Granulocyte Colony-Stimulating Factor (G-CSF), GM-CSF or Stem Cell Factor (SCF)), and 0.5 µl polymerase (2 units) as well as the buffer thereof, so as to form a final reaction volume of 25 µl. The polymerase chain reaction (PCR) was performed in a DNA thermal cycler (Perkin-Elmer-Cetus) for 35 cycles, each cycle consisting of denaturation at 94° C. for 45 sec., annealing at an appropriate temperature for 45 sec., and extension at 72° C. for 1 min. The resultant PCR products were subjected to electrophoresis on 2% agarose gels and visualized by ethidium bromide staining.

In order to compare the tested samples, normalization of the data was necessary. For this purpose, the PCR amplified products of β-actin were used as an internal standard to represent the relatively equal amounts of cDNA template subjected to PCR.

The nucleotide sequences of the primers for each of the five target cytokines under detection as well as β-actin were designed based on the information posted on the website of the National Center for Biotechnology Information (NCBI), and the sizes of the corresponding PCR products thereof were listed in Table 7.

TABLE 8

Nucleotide sequences of the primers used in the RT-PCR and the sizes of the corresponding PCR products thereof

| Cytokine | Sequence (5' to 3') | | Size of PCR product (bps) |
|---|---|---|---|
| β-actin | | | |
| forward primer | gactacctcatgaagatcct | (SEQ ID NO:1) | 510 |
| Reverse primer | ccacatctgctggaaggtgg | (SEQ ID NO:2) | |
| IL-1β | | | |
| forward primer | atggcaactgttcctgaactcaact | (SEQ ID NO:3) | 563 |
| Reverse primer | caggacaggtatagattcttcctttt | (SEQ ID NO:4) | |
| IL-6 | | | |
| forward primer | atgaagttcctctctgcaagagact | (SEQ ID NO:5) | 638 |
| Reverse primer | cactaggtttgccgagtagatctc | (SEQ ID NO:6) | |
| G-CSF | | | |
| forward primer | gcttcagctggatgttgccaa | (SEQ ID NO:7) | 216 |
| Reverse primer | tctgctcaggtctaggccaagt | (SEQ ID NO:8) | |

TABLE 8-continued

Nucleotide sequences of the primers used in the RT-PCR and the sizes of the corresponding PCR products thereof

| Cytokine | Sequence (5' to 3') | | Size of PCR product (bps) |
|---|---|---|---|
| GM-CSF | | | |
| forward primer | ttcctgggcattgtggtctac | (SEQ ID NO:9) | 430 |
| Reverse primer | tggattcagagctggcctgg | (SEQ ID NO:10) | |
| SCF | | | |
| forward primer | tcttcaactgctcctattt | (SEQ ID NO:11) | 562 |
| Reverse primer | actgctactactgctgtcattc | (SEQ ID NO:12) | |

Results:

(I). Cell Counting and Sorting of Leukocytes in Peripheral Blood:

Administration of high doses of cytotoxic chemotherapeutic agents, such as cyclophosphamide (CY), would impair the hemopoiesis of bone marrow, thus resulting in a temporary deficiency of leukocytes in the peripheral blood.

C57BL/6j mice were i.p. administered with 200 mg/kg of CY on Day 0 and were respectively given an oral treatment of 40 mg/kg, 200 mg/kg or 1000 mg/kg of PoMuM starting from Day 1. The peripheral blood samples were collected, and the numbers of total leukocytes were counted.

Figure 8:
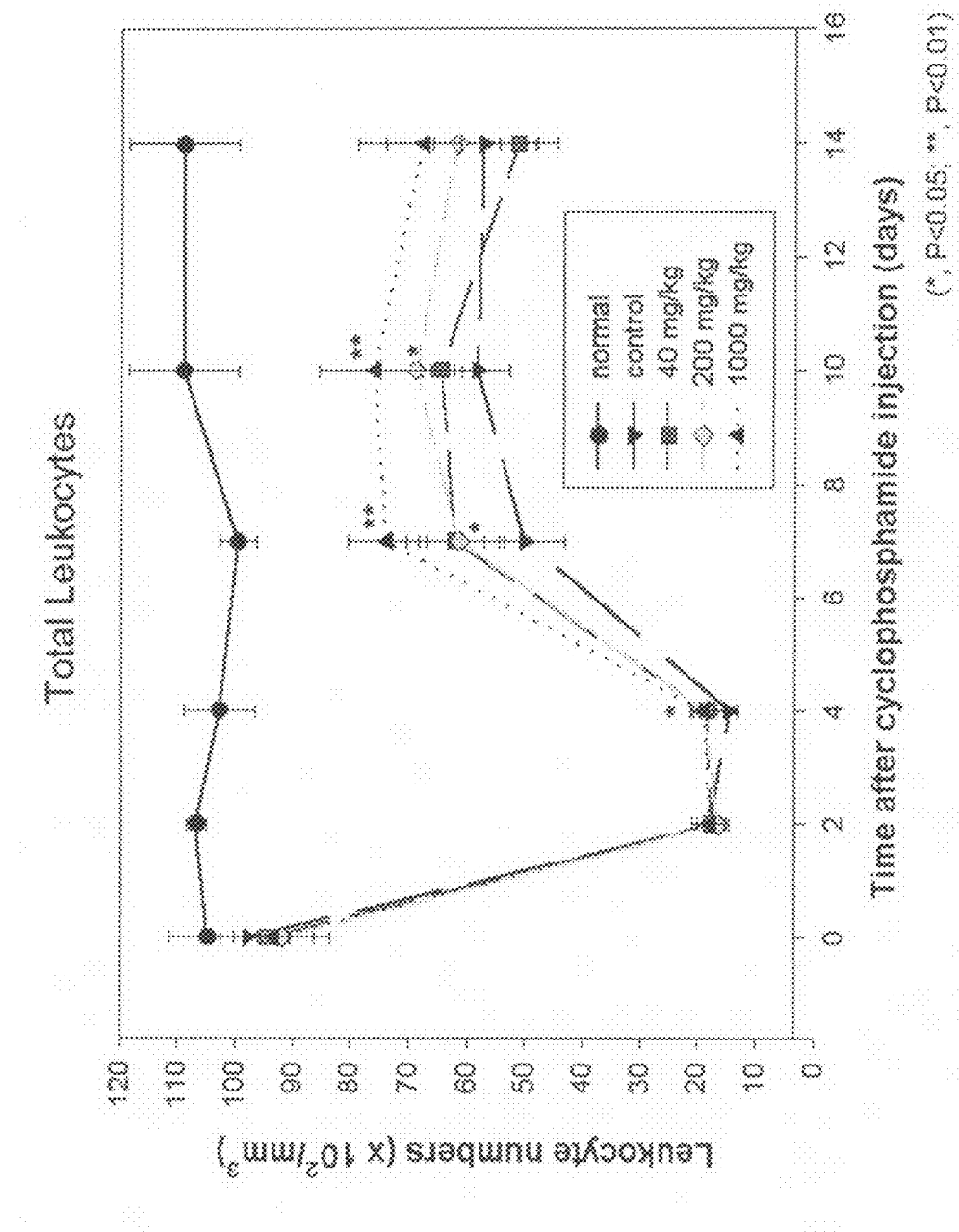
FIG. 8 shows the effect of PoMuM in promoting the recovery of leukocytes in peripheral bloods of cyclophosphamide (CY)-treated mice, in which the results were displayed as means±S.D. (n=4 to 6 for each group), and data were analyzed by Student's t-test (test group vs. control, *: $P<0.05$ and **: $P<0.01$)

Referring to FIG. 8, a single dose of CY (200 mg/Kg) to C57/BL6j mice caused the number of total leukocytes in peripheral blood to reach the nadir on Day 4. As compared with the control group, oral administration of the methanol-extracted product of *Polygonum multiflorum* root according to this invention (PoMuM) prevented the decrease and promoted the recovery of the total leukocytes in the peripheral blood of the CY-induced leukopenic mice since Day 2. Moreover, oral administration of PoMuM at a dose of either 200 or 1000 mg/kg per day caused a significant increase of the total leukocytes in the peripheral blood of the CY-induced leukopenic mice on Day 7 and Day 10.

Figure 9:
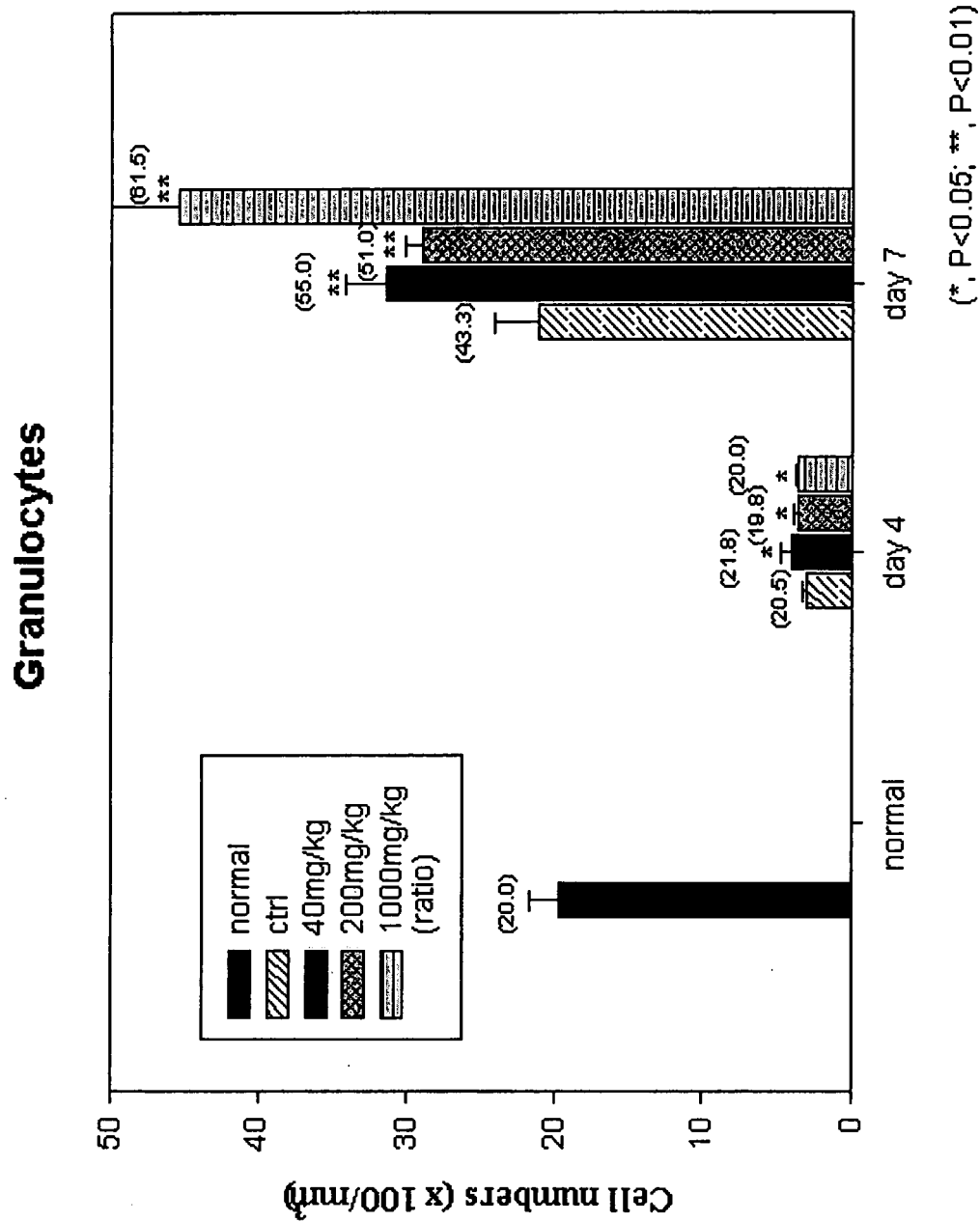
FIG. 9 is a bar diagram showing the effect of PoMuM on the cell number of granulocytes in peripheral bloods of CY-treated mice, in which the results were displayed as means±S.D. (n=4 to 6 for each group), and data were analyzed by Student's t-test (test group vs. control, *: $P<0.05$ and **: $P<0.01$)

The peripheral blood samples collected on Day 4 and Day 7 were further subjected to a differentiation count, and the obtained results are shown in FIG. 9, in which the number of granulocytes in the peripheral blood from each of the normal group, the CY-treated control group and the PoMuM-treated groups was calculated as the total cell number multiplied by the ratio of granulocyte, the numeral of which was parenthesized. Similar results were obtained in two independent experiments.

It was found that oral administration of the methanol-extracted product of *Polygonum multiflorum* root according to this invention (PoMuM) caused an increase of granulocytes as compared with the control group. In addition, the detected cell ratio of granulocyte in each of the PoMuM-treated groups was increased from 20% to 51% or higher, while the cell ratio of granulocyte in the control group only reached 43%.

In the meantime, while no significant change of the cell ratio of lymphocyte was caused by oral administration of the methanol-extracted product of *polygonum multiflorum* root according to this invention (PoMuM), it was observed that on Day 4, the detected cell number of lymphocytes in each of the PoMuM-treated groups was slightly higher than that of the control group (data not shown).

(II). GM-CSF-Stimulation Test:

On Day 5 and Day 8, the CY-treated C57BL/6j mice, which had been administered daily with different doses (0, 40, 200 and 1000 mg/kg) of PoMuM, were sacrificed, and the bone marrow cells taken therefrom were placed into 96-well culture plates at a cell density of $1 \times 10^5$ nucleated cells/well and incubated with different concentrations of mGM-CSF for 96 hours. The cell proliferation responses were measured by MTT assay, and the obtained results are shown in FIGS. 10 and 11.

Figure 10:
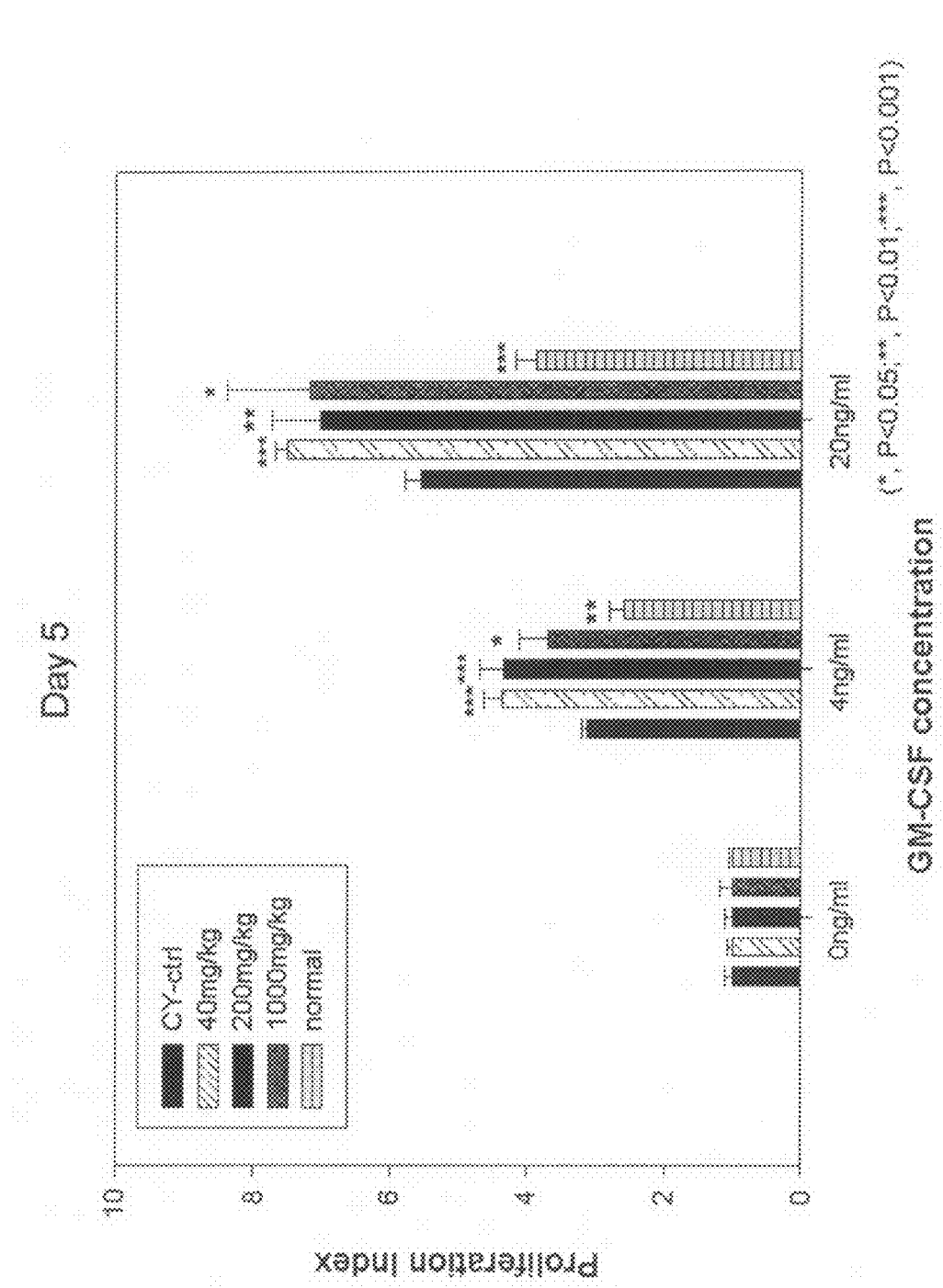
FIG. 10 is a bar diagram showing the effect of PoMuM in promoting the repopulation of mGM-CSF responsive bone marrow cells in CY-treated mice, which had been administered daily with different doses (0, 40, 200 and 1000 mg/kg) of PoMuM and sacrificed on Day 5, in which the results were displayed as means±S.D. (n=4 to 6 for each group), and data were analyzed by Student's t-test (test group vs. control, *: $P<0.05$, : $P<0.01$ and *: $P<0.001$)
Figure 11:
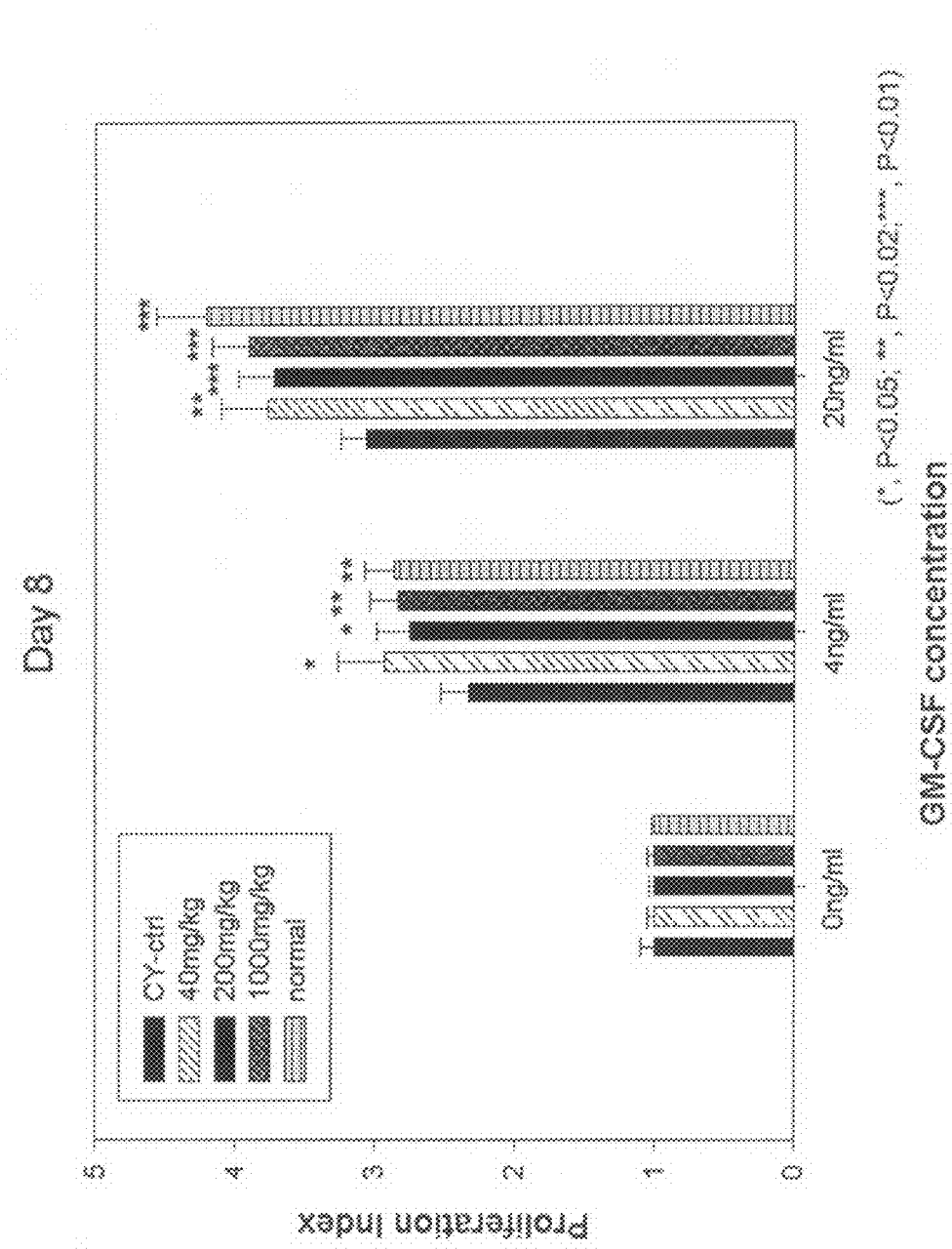
FIG. 11 is a bar diagram showing the effect of PoMuM in promoting the repopulation of GM-CSF responsive bone marrow cells in CY-treated mice, which had been administered daily with different doses (0, 40, 200 and 1000 mg/kg) of PoMuM and sacrificed on Day 8, in which the results were displayed as means±S.D. (n=4 to 6 for each group), and data were analyzed by Student's t-test (test group vs. control, *: $P<0.05$, : $P<0.02$ and *: $P<0.01$)

It can be seen from FIG. 10 that, on Day 5 (i.e. the acute response stage), an enhanced proliferation or repopulation of mGM-CSF responsive bone marrow cells by administration of different doses of PoMuM was observed. Referring to FIG. 11, on Day 8 (i.e. the plateau stage), the proliferative response of bone marrow hematogenic cells in each of the experimental group was still higher than that of the CY-control group. These data indicate that PoMuM was effective in promoting the recovery of mouse bone marrow hematogenic cells.

(III). Detection of Cytokine Expression by RT-PCR:

On Day 5, the CY-treated C57BL/6j mice, which had been administered daily with different doses (40, 200 and 1000 mg/kg) of PoMuM, were sacrificed, and total mRNAs were extracted from their bone marrow cells. The mRNAs were then reverse-transcripted and amplified using the cytokine-specific 5' and 3' primers listed in Table 8. The resultant PCR products were subjected to electrophoresis on 2% agarose gels and visualized by ethidium bromide staining. The degree of expression of each target cytokine was expressed as the ratio of the detected intensity in average of each experimental group to that of the CY-control group.

Figure 12:
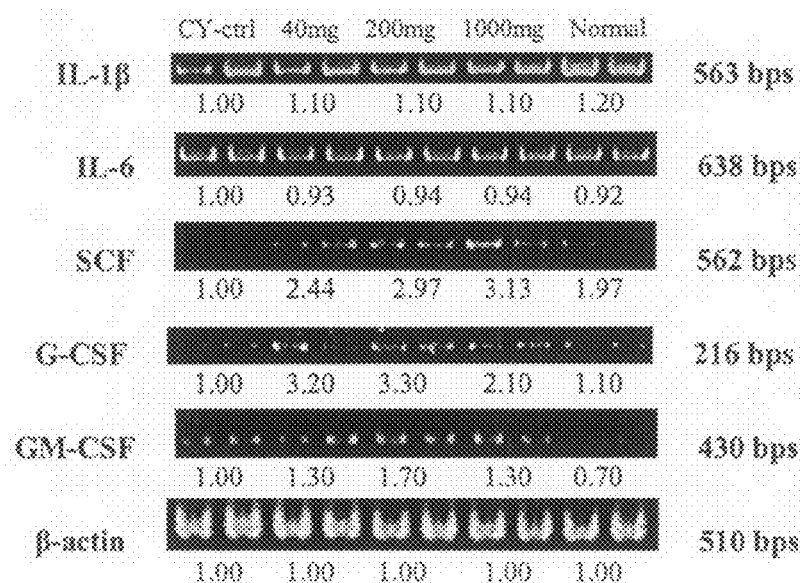
FIG. 12 shows the effect of PoMuM on the cytokine expression of bone marrow cells in CY-treated mice, in which the degree of expression of each target cytokine was expressed as the ratio of the detected intensity in average of each experimental group to that of the CY-control group.

It can be seen from FIG. 12 that the expression of hemopoietic cytokines, including GM-CSF, G-CSF and SCF, in each of the PoMuM-treated groups was significantly enhanced. The observed results further demonstrated the effect of PoMuM in promoting the recovery of mouse bone marrow hematogenic cells.

Example 10

Evaluation of the Effect of Extract of *Polygonum multiflorum* Thunb. Root on the Recovery of Hemopoiesis in Anemic Mice In Vivo This example investigates the effect of the methanol-extracted product from the root of *Polygonum multiflorum* (PoMuM) in promoting the recovery of hemopoiesis in cyclophosphamide-induced anemic mice.

Experimental Procedures:

Daily drinks containing different concentrations (40 mg/Kg, 200 mg/Kg and 1000 mg/Kg) of PoMuM were prepared in the same manner as described in Example 8.

Balb/c mice (female, 6-8 weeks old, and n=4~6 for each group) were ip. administrated with two high doses (200 mg/kg and 100 mg/kg) of cyclophosphamide (CY) on Day 0 and Day 6, respectively, so as to induce a significant impairment to the bone marrow cells of said mice, thereby resulting in the occurrence of severe anemia in said mice. These mice were fed with the respective daily drinks ad libitum starting from Day 1, and the daily drinks were replenished every two days. The normal group was ip. treated with a 0.85% NaCl solution (0.2 ml), and the control group was the CY-treated group without treatment of the tested extract product. The mice were subjected to the following tests. Each experiment was conducted in duplicate.

(I). Cell counting of erythrocytes in peripheral blood (Owen, M E. et al. (1987), *Journal of Cell Science,* 87: 731-738):

On Day 0, Day 4, Day 8, Day 12 and Day 16, 0.1 ml of peripheral blood was sampled from the orbita of each of the mice and admixed with 25 µl of an EDTA solution (72 mg/ml) so as to prevent blood coagulation. The resultant whole blood sample was subjected to RBC counting as follows:

The whole blood sample was subjected to a 2000-fold dilution with normal saline and then placed into a counting chamber for counting the number of erythrocytes under a microscope with a magnification of 400×.

(II). Hematocrit Analysis of Peripheral Blood:

An aliquot (50 µl) of whole blood was pipetted into a capillary tube with a diameter of 1.1~1.2 µm, and the tube opening was sealed by fire burning. The capillary tube was then centrifuged at 2,500 rpm for 10 minutes, and the hematocrit percentage of the tested blood was determined by calculating the ratio of the height of blood cells to the height of the total blood.

Results:

Balb/c mice were ip. administered with 200 mg/kg and 100 mg/kg of CY on Day 0 and Day 6, respectively, and periodically subjected to an extensive blood removal treatment, so as to result in the occurrence of severe anemia in said mice.

Administration of two high doses of CY would extensively impair the bone marrow cells of Balb/c mice, and the periodic removal of blood further caused a massive loss of mature RBC in the blood circulation system of said mice. As a result, an animal model of severe anemia was established.

The anemic CY-treated Balb/c mice were respectively given an oral treatment of 40 mg/kg, 200 mg/kg or 1000 mg/kg of PoMuM starting from Day 1. On Day 4, 8, 12 and 16, the peripheral blood samples were collected and subjected to RBC counting and hematocrit analysis, respectively.

Figure 13:
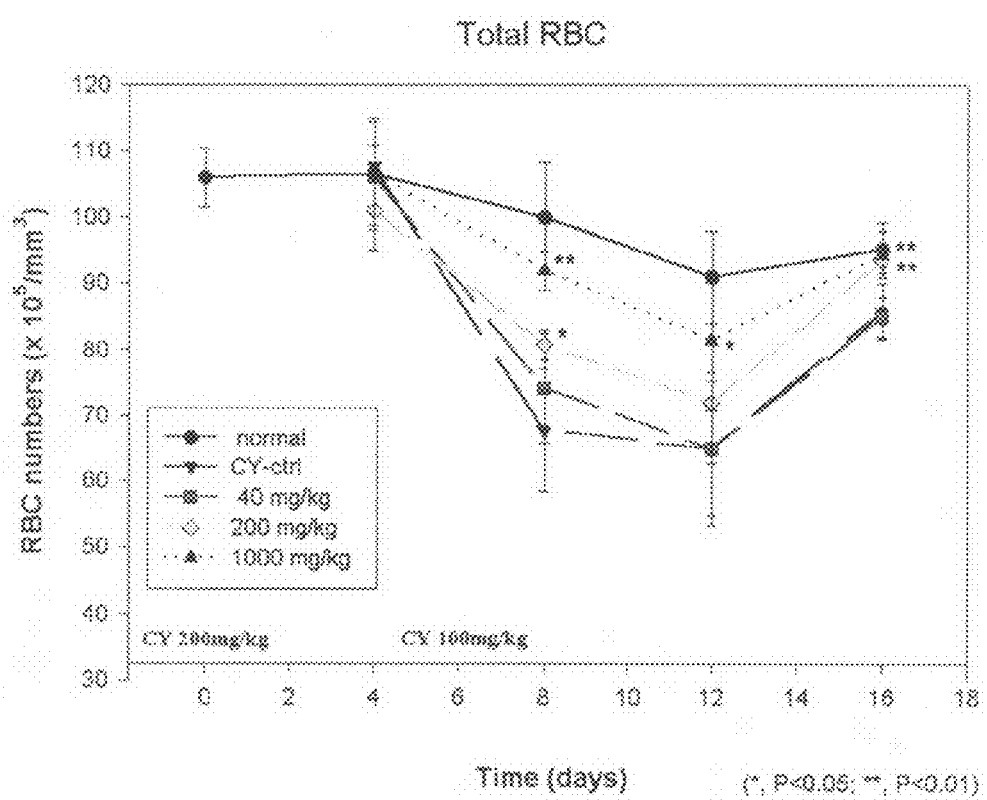
FIG. 13 shows the effect of PoMuM on the recovery of hemopoiesis in severe anemic CY-treated mice, in which the recovery was measured by total red blood cell (RBC) count in peripheral blood, and the results were displayed as means±S.D. (n=4 to 6 for each group), and data were analyzed by Student's t-test (test group vs. control, *: $P<0.05$ and **: $P<0.01$)
Figure 14:
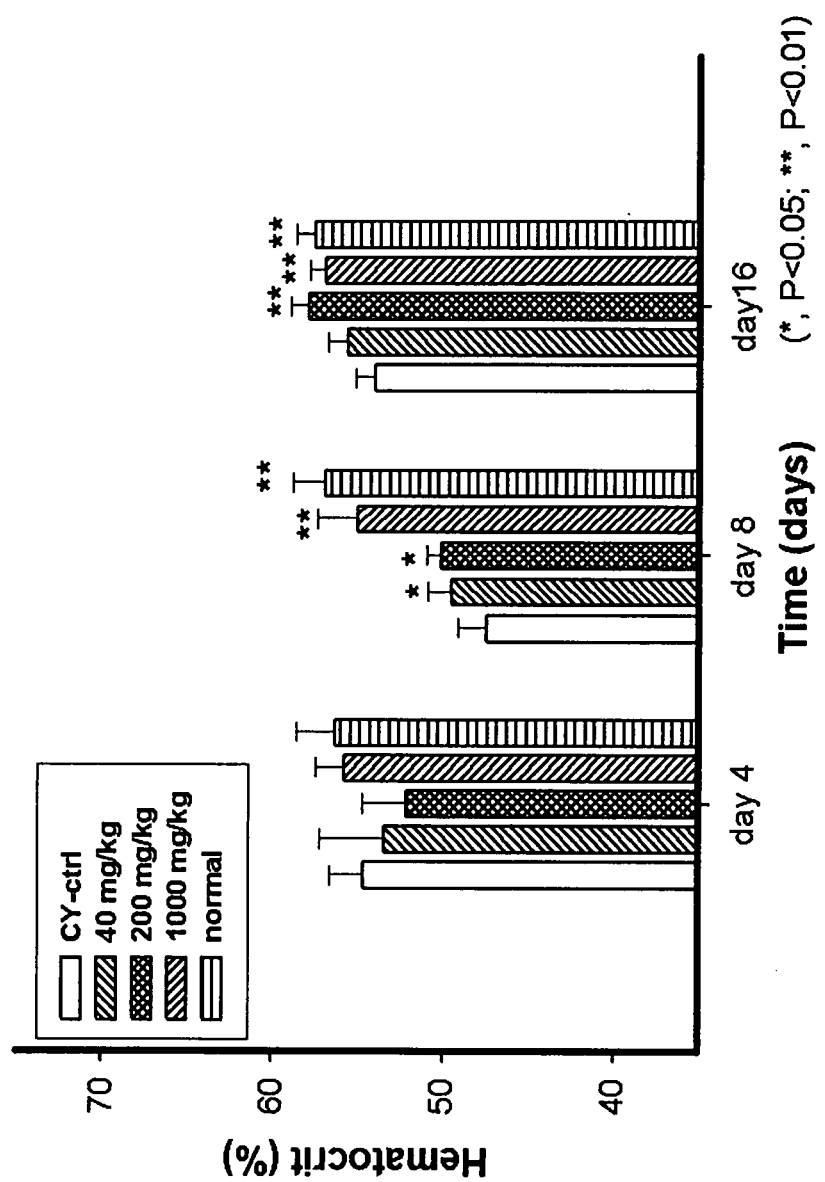
FIG. 14 shows the effect of PoMuM in promoting the recovery of hematocrit percentage in severe anemic CY-treated mice, in which the results were displayed as means±S.D. (n=4 to 6 for each group), and data were analyzed by Student's t-test (test group vs. control, *: $P<0.05$ and **: $P<0.01$).

It can be seen from FIG. 13 that a significant recovery of RBC in the peripheral blood was observed in the experimental groups orally administered with PoMuM at a daily dose of 200 mg/kg or 1000 mg/kg. Likewise, referring to FIG. 14, the experimental groups receiving an oral administration of PoMuM at a daily dose of 200 mg/kg or 1000 mg/kg were shown to have a higher hematocrit percentage as compared to that of the CY control group.

Based on the obtained results, the methanol-extracted product of *Polygonum multiflorum* Thunb. root according to this invention, which has been proved to be effective in promoting the recovery of RBC, was believed to have potential in the development of medicines for use in the treatment of disorders or diseases associated with RBC deficit.

All patents and literature references cited in the present specification are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

The embodiments of the invention in which an exclusive property or privilege is claimed are defined as follows:

1. A method for treating anemia or leukopenia in a subject in need thereof, comprising administering to the subject an extract product from the root of *Polygonum multiflorum* Thunb. in an amount effective to promote the proliferation of a cell type selected from the group consisting of hepatocytes, bone marrow stem cells, bone marrow stromal cells, bone marrow hematopoietic progenitor cells, bone marrow hematogenic cells, leukocytes, and erythrocytes, wherein the extract product from the root of *Polygonum multiflorum* Thunb. is a methanol extract.

2. The method of claim 1, wherein the methanol extract is prepared by a process comprising:
   (a) subjecting a starting root material of *Polygonum multiflorum* Thunb. to a freezing treatment for a period of time to obtain a frozen product;
   (b) subjecting the frozen product obtained in step (a) to methanol extraction;
   (c) subjecting the methanol extracted product from step (b) to a separating treatment to obtain a methanol solution free of extracted root debris of the starting root material of *Polygonum multiflorum* Thunb.; and
   (d) removing methanol from the methanol solution obtained in step (c) to obtain the extract product.

3. The method of claim 2, wherein the extract product obtained from step (d) is further lyophilized.

4. The method of claim 2, wherein the extract product from the root or *Polygonum multiflorum* Thunb. is administered to the subject in need thereof at a dosage of 20 mg/kg to 1,000 mg/kg per day.

5. The method of claim 1, wherein the extract product from the root of *Polygonum multiflorum* Thunb. is administered to the subject in need thereof in a pharmaceutical composition as at least one of an oral preparation, an injection, an inhalant, or nasal drops.

* * * * *